United States Patent
So

(10) Patent No.: US 12,131,477 B2
(45) Date of Patent: Oct. 29, 2024

(54) COMPUTER LEARNING ASSISTED BLOOD FLOW IMAGING

(71) Applicant: London Health Sciences Centre Research Inc., London (CA)

(72) Inventor: Aaron So, Ontario (CA)

(73) Assignee: London Health Sciences Centre Research Inc., London (CA)

( * ) Notice: Subject to any disclaimer, the term of this patent is extended or adjusted under 35 U.S.C. 154(b) by 0 days.

(21) Appl. No.: 18/626,293

(22) Filed: Apr. 3, 2024

(65) Prior Publication Data

US 2024/0331159 A1    Oct. 3, 2024

Related U.S. Application Data

(60) Provisional application No. 63/493,927, filed on Apr. 3, 2023.

(51) Int. Cl.
| | |
|---|---|
| G06T 7/00 | (2017.01) |
| G06T 7/246 | (2017.01) |
| G16H 50/30 | (2018.01) |

(52) U.S. Cl.
CPC ............ G06T 7/0016 (2013.01); G06T 7/248 (2017.01); G16H 50/30 (2018.01);
(Continued)

(58) Field of Classification Search
CPC ................... G06T 7/0016; G06T 7/248; G06T 2207/20081; G06T 2207/30104;
(Continued)

(56) References Cited

U.S. PATENT DOCUMENTS

| | | |
|---|---|---|
| 6,745,066 B1 | 6/2004 | Lin et al. |
| 7,689,267 B2 | 3/2010 | Prince |

(Continued)

FOREIGN PATENT DOCUMENTS

| | | |
|---|---|---|
| CN | 104688259 A | 6/2015 |
| WO | WO 03/046796 A2 | 6/2003 |

(Continued)

OTHER PUBLICATIONS

International Search Report and Written Opinion for Application No. PCT/CA2019/050668 mailed Sep. 5, 2019, in 10 pages.

(Continued)

*Primary Examiner* — Shefali D Goradia
(74) *Attorney, Agent, or Firm* — Knobbe, Martens, Olson & Bear, LLP

(57) ABSTRACT

Described herein is blood flow imaging based on an area under a time-enhancement curve predicted by a computer learning model. Image data comprising a plurality of corresponding images capturing at least a portion of one or both an increase phase and a decline phase of a contrast agent in a cardiovasculature of interest is inputted to a machine learning model to predict an area under a time-enhancement curve of the contrast agent within the cardiovasculature of interest, the predicted area under the time-enhancement curve representing the total sum of contrast agent concentration time product within the cardiovasculature of interest. In an example, a computer implemented method for blood flow imaging comprising: obtaining image data comprising a plurality of corresponding images capturing at least a portion of one or both an increase phase and a decline phase of a contrast agent in a cardiovasculature of interest; providing the image data to a machine learning model to predict an area under a time-enhancement curve of the contrast agent within the cardiovasculature of interest; determining a (Continued)

blood flow characteristic through the region of interest based on the area under the time-enhancement curve. Systems and non-transitory computer-readable media for executing the method are also described.

20 Claims, 30 Drawing Sheets

(52) U.S. Cl.
CPC ............ *G06T 2207/10081* (2013.01); *G06T 2207/10088* (2013.01); *G06T 2207/20081* (2013.01); *G06T 2207/30104* (2013.01)

(58) Field of Classification Search
CPC ........... G06T 2207/10088; G06T 2207/10081; G16H 50/30
See application file for complete search history.

(56) References Cited

U.S. PATENT DOCUMENTS

| | | |
|---|---|---|
| 8,792,701 B2 | 7/2014 | Djeridane et al. |
| 8,929,632 B2 | 1/2015 | Horz et al. |
| 9,174,065 B2 * | 11/2015 | Gertner .................. A61N 5/062 |
| 9,433,392 B2 | 9/2016 | Ohishi |
| 10,192,640 B2 | 1/2019 | Itu et al. |
| 10,463,336 B2 | 11/2019 | Itu et al. |
| 10,580,131 B2 | 3/2020 | Mazo |
| 10,748,289 B2 | 8/2020 | Tolkowsky et al. |
| 10,762,637 B2 | 9/2020 | Gulsun et al. |
| 10,984,531 B2 | 4/2021 | Klaiman et al. |
| 11,216,950 B2 | 1/2022 | Cho et al. |
| 11,315,293 B2 | 4/2022 | Siemionow et al. |
| 11,389,130 B2 | 7/2022 | Itu et al. |
| 11,490,867 B2 | 11/2022 | Homann et al. |
| 11,521,322 B2 | 12/2022 | Siemionow et al. |
| 2007/0167731 A1 * | 7/2007 | Taxt .................. G01R 33/56366 600/410 |
| 2008/0119715 A1 * | 5/2008 | Gonzalez Molezzi ...................... A61B 6/481 600/407 |
| 2011/0150309 A1 | 7/2011 | Barfett et al. |
| 2013/0172734 A1 | 7/2013 | Hsieh |
| 2014/0114185 A1 * | 4/2014 | Tolkowsky ............ A61B 6/504 600/431 |
| 2015/0087956 A1 * | 3/2015 | Yao ........................ A61B 6/022 600/407 |
| 2017/0007195 A1 | 1/2017 | Molloi |

FOREIGN PATENT DOCUMENTS

| | | | |
|---|---|---|---|
| WO | WO 2005/044104 A1 | 5/2005 | |
| WO | WO 2010/045003 A1 | 4/2010 | |
| WO | WO-2010045478 A2 * | 4/2010 | ........... A61B 5/0263 |
| WO | WO 2019/218076 A1 | 11/2019 | |
| WO | WO 2022/040806 A1 | 3/2022 | |

OTHER PUBLICATIONS

International Search Report and Written Opinion for Application No. PCT/CA2021/051189 mailed Nov. 30, 2021, in 10 pages.

* cited by examiner

Time 0     Time 0 + Δt

Time 0     Time 0 + Δt

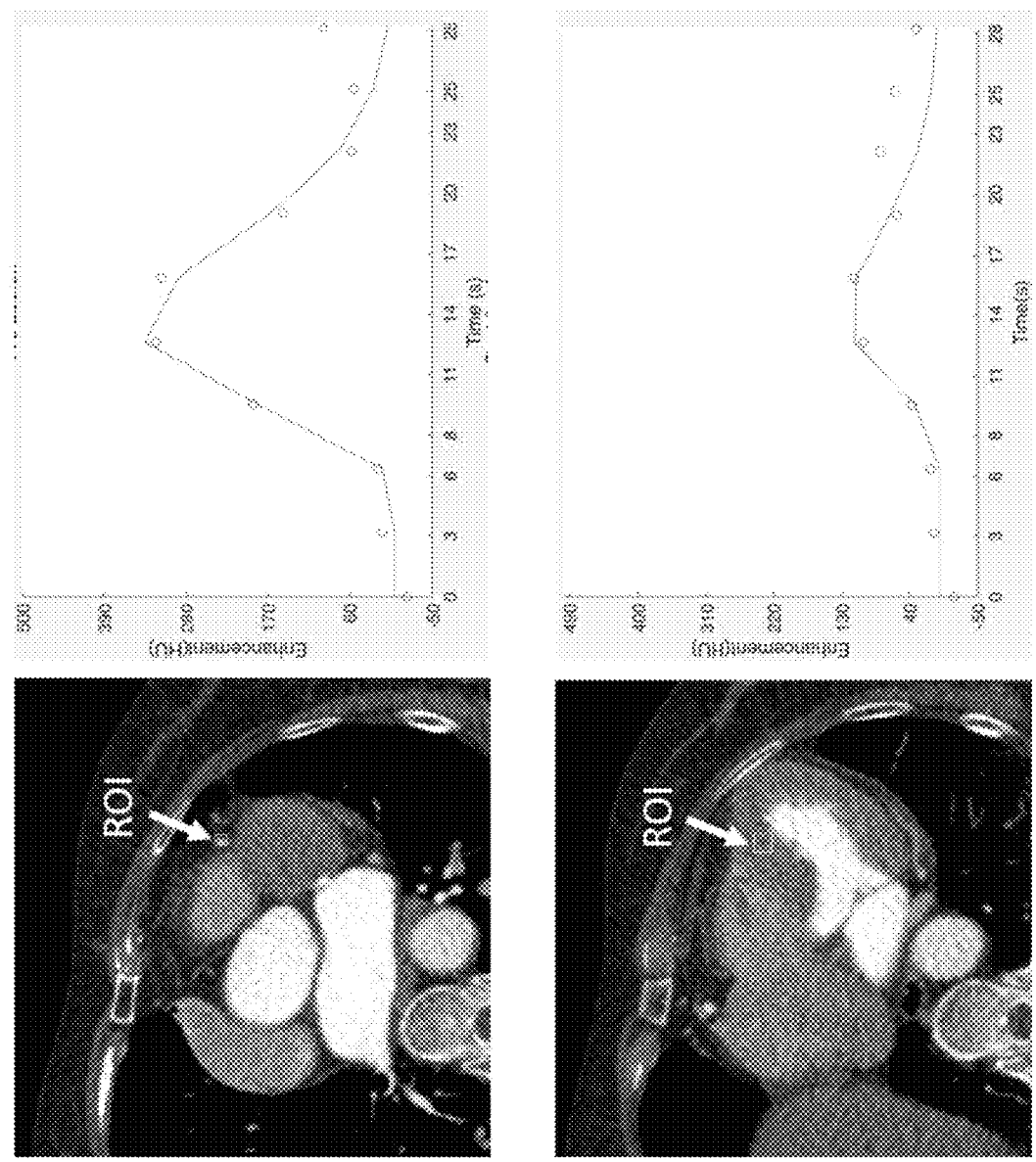
FIGURE 23
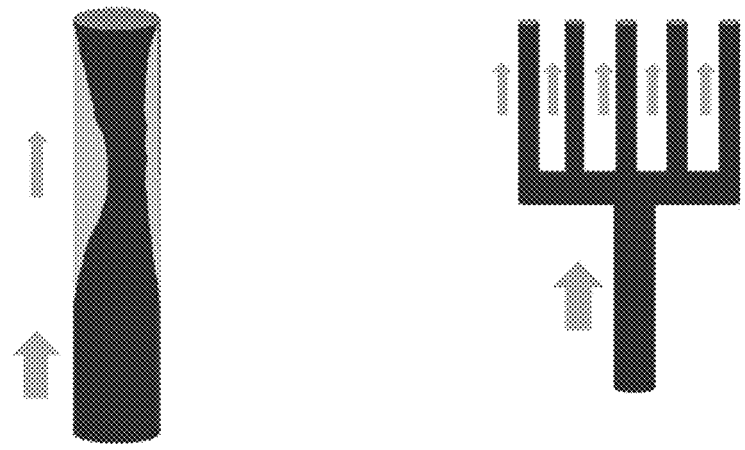

STRESS

REST

FIGURE 29 train loss : 153.37985
train r2_score: 0.9048733
test loss : 302.23795
test r2_score: 0.837042

FIGURE 35A
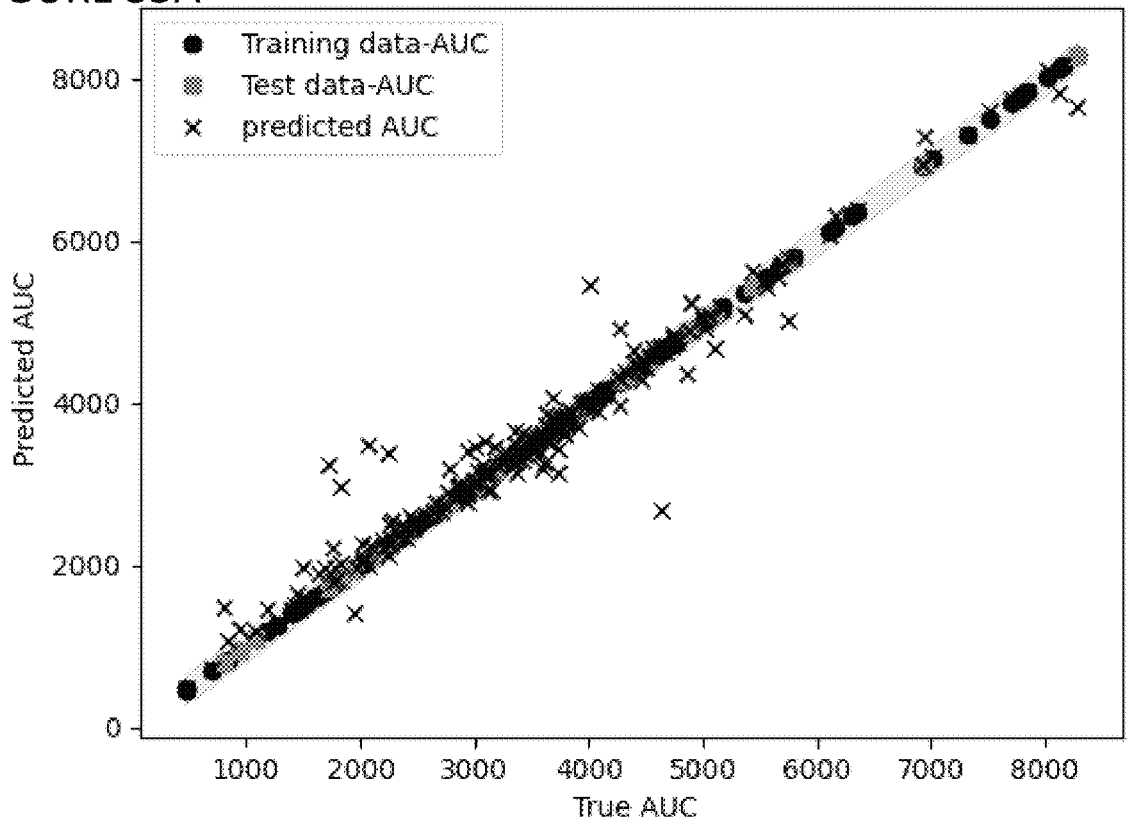
FIGURE 35B
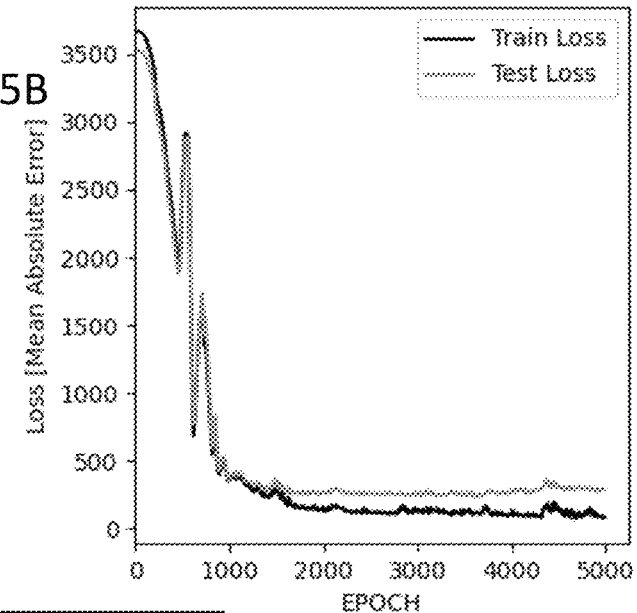
FIGURE 35C
train loss : 8.315097
train r2_score: 0.9969506
test loss : 234.72777
test r2_score: 0.9430755

FIGURE 38A
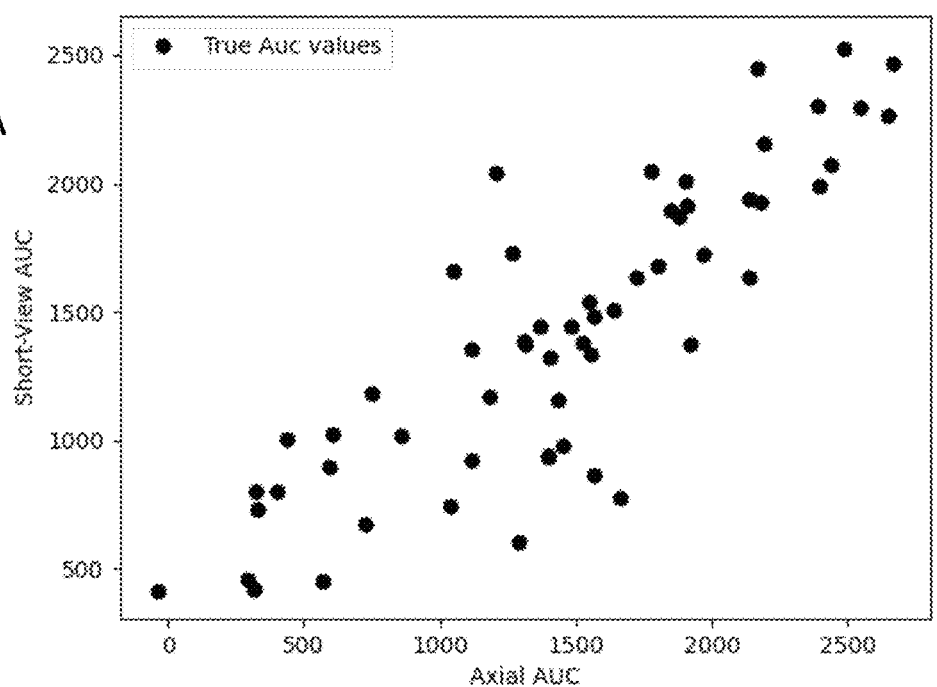
FIGURE 38B
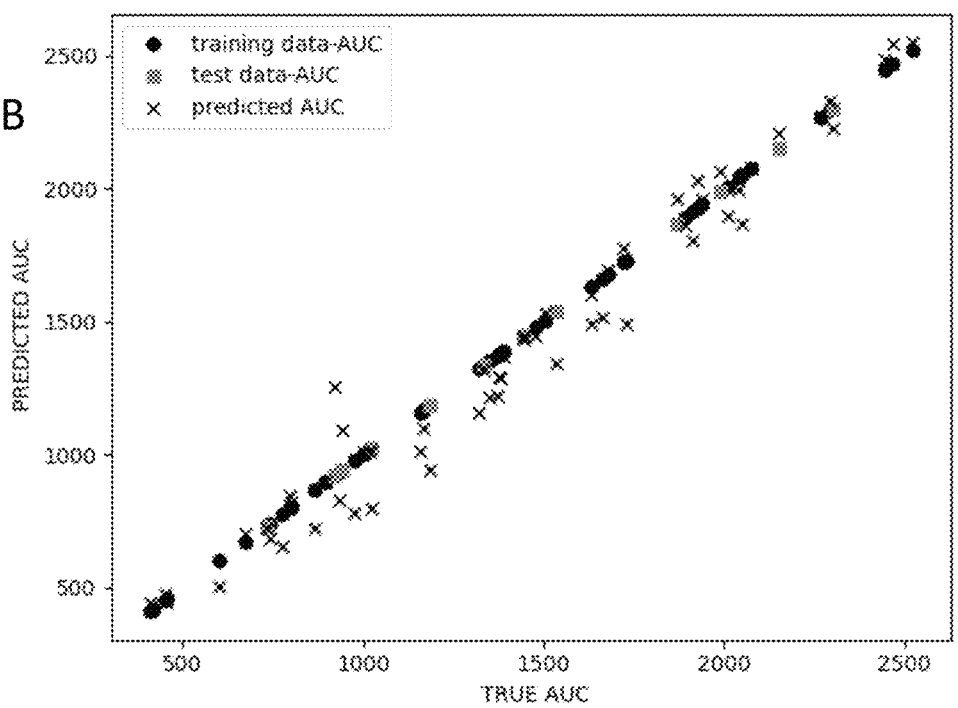
FIGURE 38C

FIGURE 39A
FIGURE 39B
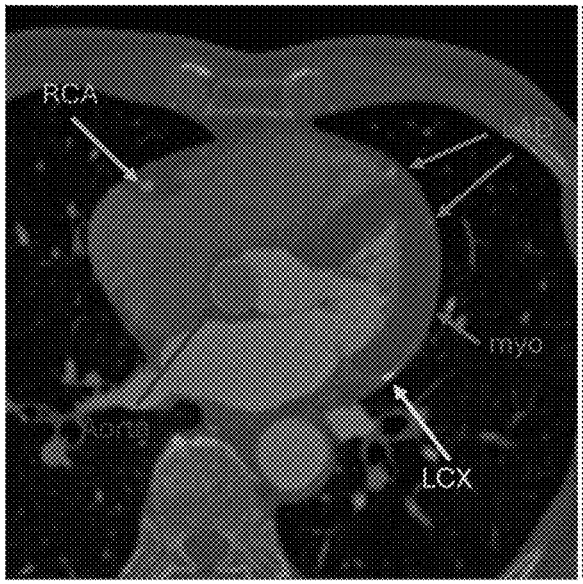
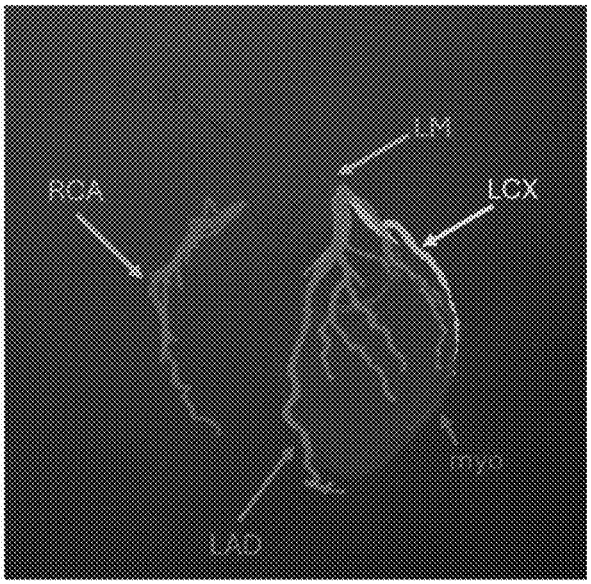
FIGURE 39C

COMPUTER LEARNING ASSISTED BLOOD FLOW IMAGING

BACKGROUND OF THE INVENTION

Field of the Invention

The present invention relates to dynamic imaging of flow, and more particularly to assessment of a blood flow characteristic in a subject based on dynamic imaging of contrast agent flow through a blood vessel or heart structure.

Description of the Related Art

Dynamic contrast-enhanced (DCE) computed tomography (CT) has been used to assess blood flow and flow pressure in blood vessels, for example as described in co-owned International PCT Application No. PCT/CA2019/050668 filed 16 May 2019 (published as WO2019/218076 on 21 Nov. 2019), incorporated herein by reference. In this disclosure, Indicator Dilution Principle is used for blood flow assessment derived from DCE CT representing average values over the course of many seconds of imaging scans, often greater than 10 seconds, and therefore does not have sufficient temporal resolution to achieve 4D flow imaging, that is, to track a blood flow characteristic in selected image voxels at very fine temporal resolution, for example calculating changes in flow velocity at time intervals of less than 1 second.

An improvement with respect to fine temporal resolution is described in co-owned International PCT Application No. PCT/CA2021/051189 filed 26 Aug. 2021 (published as WO2022/040806 on 3 Mar. 2022), incorporated herein by reference. In this disclosure, Indicator Dilution Principle and Reynolds Transport Theorem are used to substantially improve the temporal resolution of non-invasive blood flow assessment with DCE CT imaging data.

These two disclosures improved upon the existing state of CT imaging, and introduced novel extractions and implementations of parameters from a time-enhancement curve at a region of interest, including for example, area-under-curve, time rate of change of tracer mass in the region of interest, or density of tracer in blood in the region of interest.

As diagnostic imaging is a very active area of clinical workflow, further improvement is welcomed by medical practitioners including for example, improvement in computer efficiency, reduction of radiation dose, or improvement in accuracy.

Accordingly, there is a continuing need for alternative methods and systems for blood flow imaging based assessment of a blood vessel in a subject.

SUMMARY OF THE INVENTION

In an aspect there is provided a computer implemented method for blood flow imaging comprising:
  obtaining CT or MRI image data comprising a plurality of corresponding images capturing at least a portion of one or both an increase phase and a decline phase of a contrast agent in a cardiovasculature of interest;
  extracting a first image feature of a measured time-enhancement curve from the CT or MRI image data;
  providing the first image feature and at least one non-image feature to a machine learning model to generate a predicted value of an area under a simulated time-enhancement curve of the contrast agent within the cardiovasculature of interest, the predicted value simulating a second set of image acquisition parameters that are different than a first set of image acquisition parameters used to acquire the CT or MRI image data;
  converting the predicted value of area under the simulated time-enhancement curve to a total sum of contrast agent concentration time product in the cardiovasculature of interest;
  determining a blood flow characteristic in the cardiovasculature of interest based on a ratio of mass of the contrast agent in the cardiovasculature of interest to a total sum of contrast agent concentration time product in the cardiovasculature of interest.

A further related example of the method, further comprises including a baseline data point extracted from the CT or MRI image data in the measured time-enhancement curve, the CT or MRI image data comprises at least one image capturing the cardiovasculature of interest prior to entry of the contrast agent to provide the baseline data point.

In a further related example of the method, the machine learning model is trained with training inputs of the image feature of the measured time-enhancement curve and at least one non-image feature, and associated with a ground truth value of an expected area under the simulated time-enhancement curve.

In a further related example of the method, the image feature is an at least partial time-enhancement curve and extracting the image feature comprises: generating the at least partial time-enhancement curve of the contrast agent based on the image data, the at least partial time-enhancement curve having at least an upslope or a downslope. The at least partial time-enhancement curve may be any suitable truncated or full time-enhancement curve.

In a further related example of the method, the image feature is a measured value of an area under an at least partial time-enhancement curve and extracting the image feature comprises: generating the at least partial time-enhancement curve of the contrast agent based on the image data, the at least partial time-enhancement curve having at least an upslope or a downslope; and calculating the area under the at least partial time-enhancement curve. The at least partial time-enhancement curve may be any suitable truncated or full time-enhancement curve.

In a further related example of the method, the method further comprises providing a second image feature based on enhancement of signal intensity, thickness of a wall of a cardiovasculature of interest, size of a cardiovasculature of interest, diameter of a cardiovasculature of interest, morphology of a cardiovasculature of interest, location of sampling site in a cardiovascular of interest, or degree of stenosis in a cardiovasculature of interest.

In a further related example of the method, the non-image feature is based on age, sex, weight, heart rate, blood pressure, x-ray tube voltage, x-ray tube current, gradient pulse sequence, contrast-injection rate, contrast agent volume, or contrast agent concentration.

In a further related example of the method, the first set of image acquisition parameters is different than the simulated second set of image acquisition parameters according to at least one parameter selected from the group consisting of: scan projection axis, anatomical location of scan, hyperemic or rest condition of a subject, time duration of scan, x-ray tube voltage, x-ray tube current, gradient pulse sequence, contrast-injection rate, contrast agent volume, or contrast agent concentration.

In a further related example of the method, determining the blood flow characteristic comprises determining an absolute flow velocity using Reynolds transport theorem by determining a time rate of change of contrast agent mass in the cardiovasculature of interest based on a time rate of change of signal enhancement measured from an at least partial time-enhancement curve, a factor for converting signal enhancement to contrast agent concentration, a predetermined volume value of injected contrast agent, and a time value of a duration of time that signal intensity is higher than a predetermined baseline threshold level;

determining density of the contrast agent in the cardiovasculature of interest based on the ratio defined in claim 1, a time value of a duration of time that signal intensity is higher than a predetermined baseline threshold level, and the mass of contrast agent in the cardiovasculature of interest; and determining an area measured from the image data in the cardiovasculature of interest.

In a further related example of the method, determining the blood flow characteristic comprises determining a flow pressure by applying Bernoulli's equation.

In another aspect there is provided, a computer implemented method for blood flow imaging based on predicting an area under a time-enhancement curve, the method comprising:

obtaining image data comprising a plurality of corresponding images capturing at least a portion of one or both an increase phase and a decline phase of a contrast agent in a cardiovasculature of interest;

providing the image data to a machine learning model to predict an area under a time-enhancement curve of the contrast agent within the cardiovasculature of interest, the predicted area under the time-enhancement curve representing the total sum of contrast agent concentration time product within the cardiovasculature of interest.

In a further aspect there is provided a computer implemented method for blood flow imaging comprising:

obtaining image data comprising a plurality of corresponding images capturing at least a portion of one or both an increase phase and a decline phase of a contrast agent in a cardiovasculature of interest;

providing the image data to a machine learning model to predict an area under a time-enhancement curve of the contrast agent within the cardiovasculature of interest;

selecting a region of interest within the cardiovasculature of interest in the image data; determining a blood flow characteristic through the region of interest based on the area under the time-enhancement curve.

In other aspects, systems and non-transitory computer-readable media for executing the method are also provided.

BRIEF DESCRIPTION OF THE DRAWINGS

FIG. 8A shows a schematic representation of a control volume and its control surfaces; FIG. 8B shows a schematic representation of movement of fluid with respect to a control volume.

FIG. 9A shows image acquisition and reconstruction at the same cardiac phase (e.g. 75% R-R interval or diastole) over multiple time points. FIG. 9B shows image acquisition covering a full cardiac cycle (systole and diastole); multiple image sets corresponding to different cardiac phases are reconstructed.

FIG. 23 shows time-enhancement curve measured from the left anterior descending (LAD) artery (top row) and the myocardium perfused by the LAD (bottom row) in the same patient.

FIG. 29 shows two sections of Python codes. The top section shows three hidden layers were implemented in the neural network (L1, L2 and L3). No activation was specified in the output layer (last code line in the top section), which means a linear regression was used. By default, a(x)=x, where a is the activation function and x=w1b1+w2b2+ . . . , where w are the weights and b are the parameters. The codes shown in the bottom section were used to execute the neural network layers defined above.

FIG. 35A shows AUCs (depicted by crosses) of full coronary time-enhancement curves predicted by the trained machine learning model in comparison to the AUCs of full time-enhancement curves measured from full dynamic perfusion scans. The training (circle) and test (square) datasets are provided in the background. A substantial overlap between the crosses and the training/test datasets showed that accurate prediction about the full AUCs was made by the trained model. FIG. 35B shows train loss and test loss of the machine learning model as a function of epoch (number of complete passes through the entire training datasets). The train and test losses in the flat portion of the plots were low and close to each other, suggesting that the training data was not overfitted by the model. FIG. 35C shows the train and test loss and score returned by the model.

FIG. 38A shows measured short-axis AUC values plotted against measured axial AUC values (circle dots). FIG. 38B shows predicted short-axis AUC values (crosses) in comparison to the measured AUC values used for training (circles) and test (squares). FIG. 38C shows Train/Test losses and scores associated with the model training.

FIG. 39A shows feature-labeled contrast-enhanced cardiac CT images in a 2D view and FIG. 39B shows a corresponding 3D view. FIG. 39C shows MATLAB codes used for implementing a three-dimensional U-NET architecture for segmenting the cardiac CT volumetric image sets shown in FIG. 39A and FIG. 39B. The settings used for training the U-NET are also shown.

DETAILED DESCRIPTION OF PREFERRED EMBODIMENTS

With reference to the drawings, a system and method for blood flow imaging is described. The system and method compare favourably with current blood flow imaging techniques.

Figure 1:
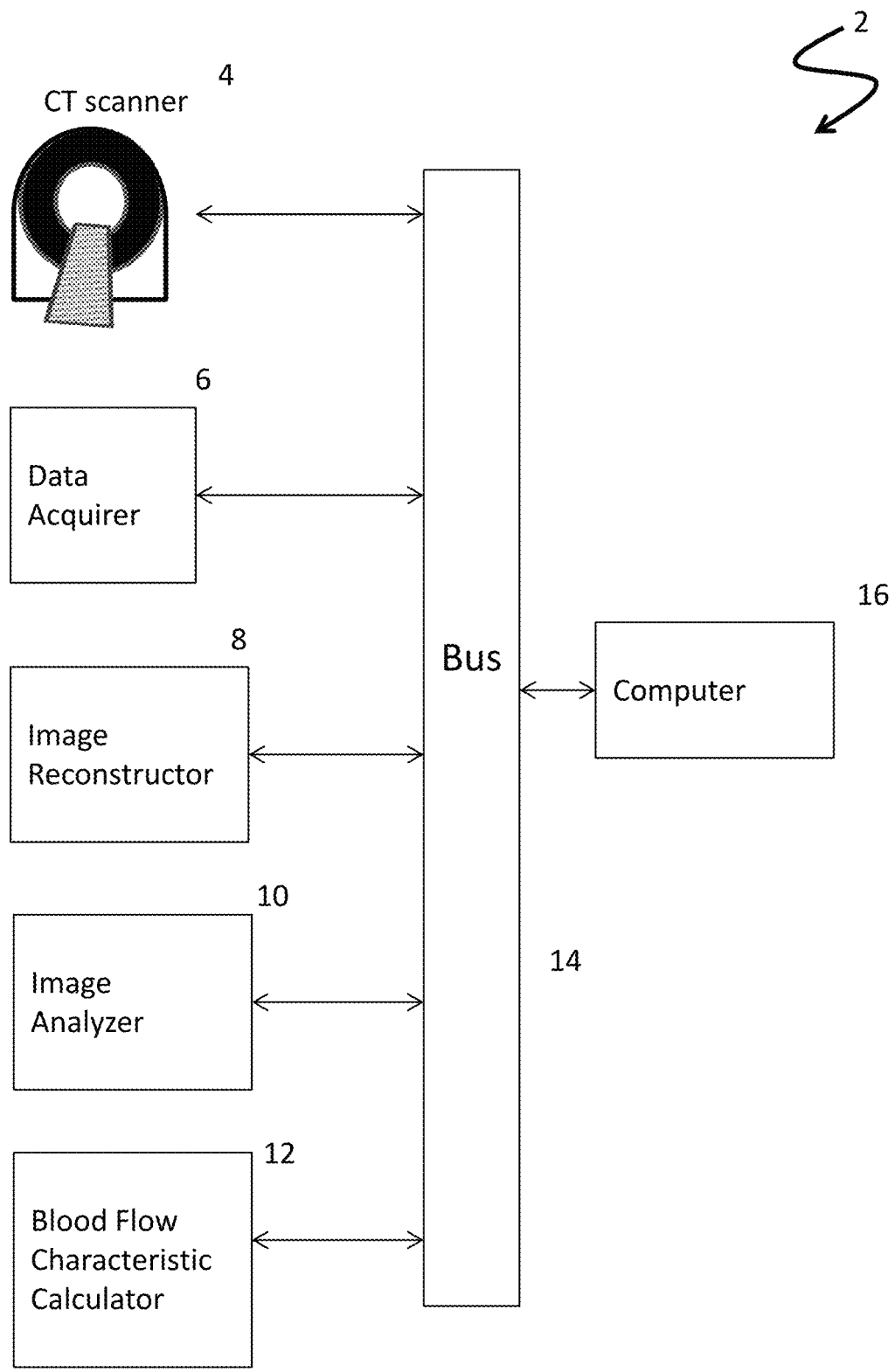
FIG. 1 shows a schematic of a blood flow imaging system.

FIG. 1 shows a computer implemented imaging system 2, incorporating a computed tomography (CT) scanner 4. The CT scanner 4 may be any multi-row or multi-slice CT scanner typically comprising a radiation source and a radiation detector disposed in a gantry and an adjustable, often motorized, support or table for maintaining a subject in a desired position (for example, a prone or supine position) in an open central chamber formed in the gantry during a scan procedure. The radiation source generates radiation that traverses one or more predetermined sampling sites targeting a blood vessel of interest in the subject in synchronization with a contrast agent (also referred to as a tracer) administered to the subject. The radiation detector, often configured as a panel of rotating detectors, receives radiation that traverses the subject at the predetermined sampling site(s) providing projection data (also referred to as scan data) over a time range that encompasses the increase phase and also optionally the decrease phase of contrast agent flowing through the blood vessel of interest.

The imaging system 2 includes a data acquisition component 6 incorporating a data acquisition scheme or data acquisition computer code that receives, organizes and stores projection data from the radiation detector of the CT scanner. The projection data is sent to an image reconstruction component 8 incorporating an image reconstruction computer code. The projection data can then be processed using the image reconstruction computer code resulting in image data including multiple images of the predetermined sampling site(s) spanning the increase phase and also optionally the decrease phase of contrast agent flowing through the blood vessel of interest. The image reconstruction computer code can easily be varied to accommodate any available CT imaging technique. The image data can then be processed by an image analysis component 10 incorporating image analysis computer code that generates a time-enhancement curve of the contrast signal from the image data. The time-enhancement curve data can then be processed by a blood flow estimation component 12 incorporating a blood flow estimation computer code to determine a blood flow characteristic of the blood vessel of interest from the time-enhancement curve data. The imaging system 2 is controlled by a computer 16 with data and operational commands communicated through bus 14. The imaging system 2 may include any additional component as desired to assess a blood vessel of interest including multiplexers, digital/analog conversion boards, microcontrollers, physical computer interface devices, input/output devices, display devices, data storage devices and the like. The imaging system 2 may include controllers dedicated to different components of the CT scanner 4, such as a radiation source controller to provide power and timing signals to control the radiation source, a gantry controller to provide power and timing signals to a gantry motor to control rotation of the gantry and thereby control rotation of the radiation source and detector, and a table controller to provide power and timing signals to a table motor to control table position and thereby control position of a subject in the gantry by moving the subject along a z-axis through an opening of the gantry communicative with the interior open chamber of the gantry. The imaging system 2 is shown with a CT scanner as an illustrative example only, and the system may be modified to include other imaging modalities, including for example, non-CT X-ray imaging or MRI.

Figure 2:
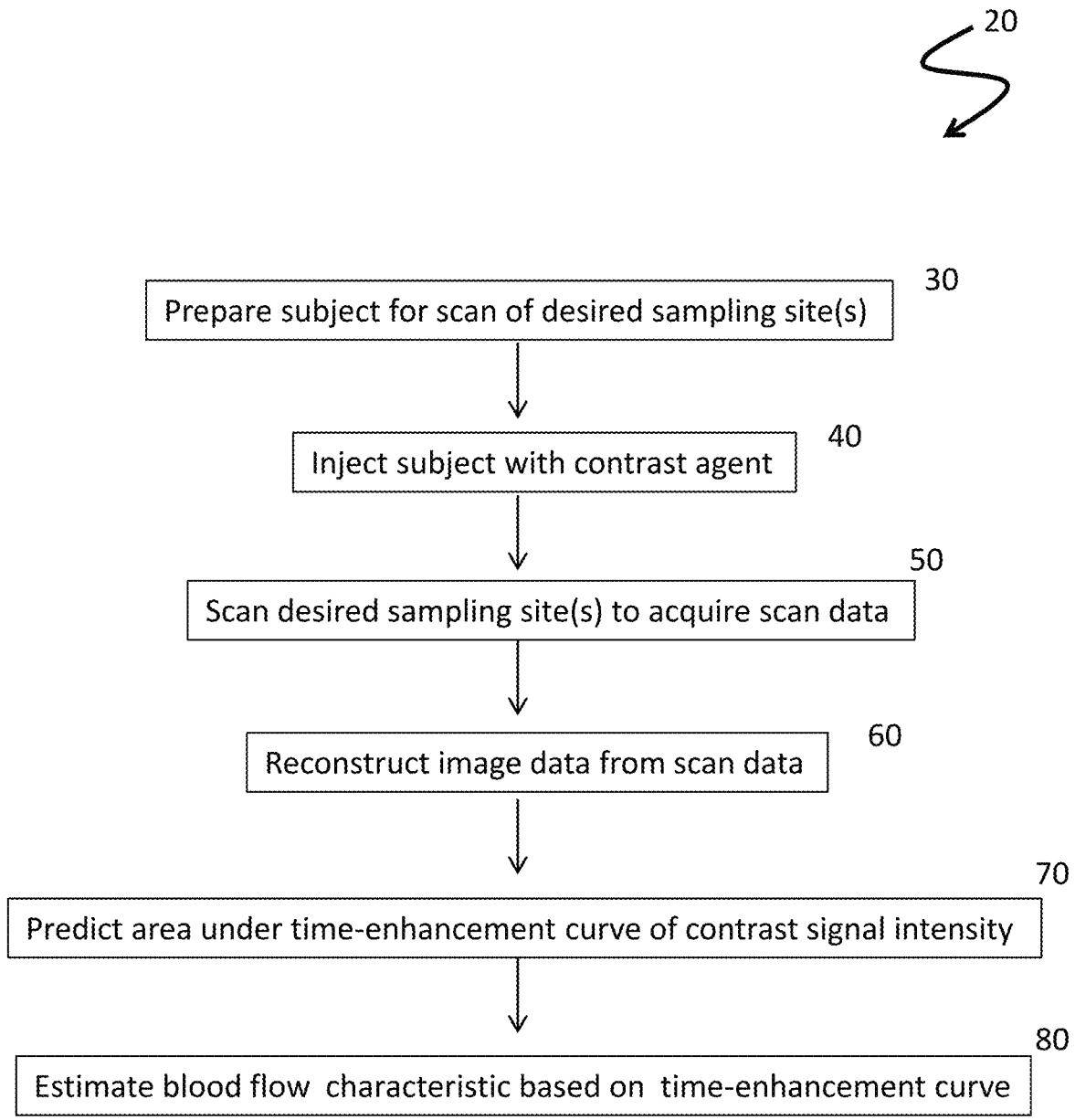
FIG. 2 shows a flow diagram of a blood flow imaging method.

FIG. 2 shows a computer implemented method 20 for blood flow imaging. The method 20 comprises a pre-scan preparation 30 and positioning of a subject for CT scanning of a desired sampling site. Once the subject is prepared and positioned within a CT scanner, the subject is injected 40 with a contrast agent solution, with CT scanning 50 synchronized with the injection of the contrast agent solution to acquire projection data (also referred to as scan data) over a time range that includes flow of the contrast agent through a blood vessel at the sampling site. The projection data is processed to reconstruct 60 image data from the projection data. The image data is analyzed to predict 70 an area under a time-enhancement curve of a contrast signal parameter, such as contrast signal intensity, extracted from the image data. A blood flow value is calculated 80 based on the time-enhancement curve.

Figure 3:
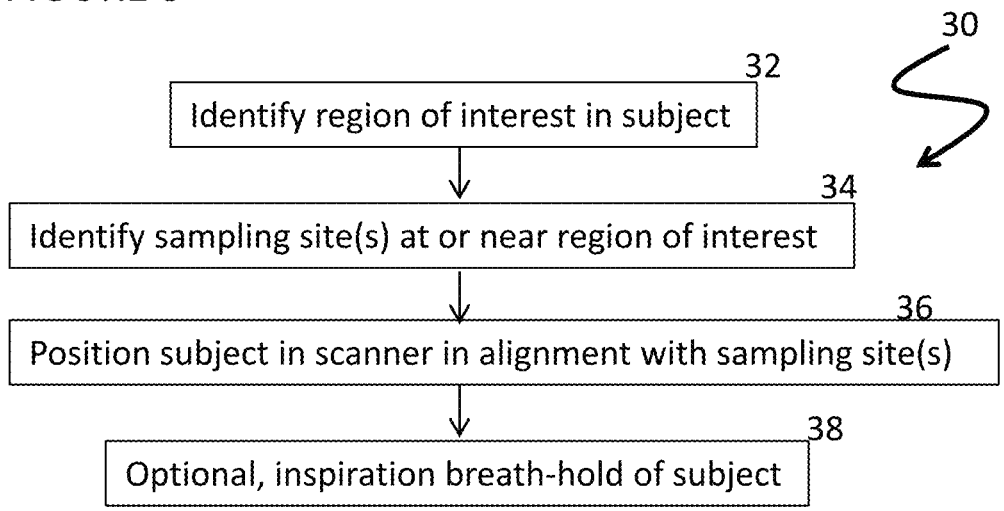
FIG. 3 shows a flow diagram of a pre-scan preparation in the imaging method shown in FIG. 2.

FIG. 3 shows an example of a pre-scan preparation 30 of a subject for CT scanning. The pre-scan preparation 30 includes identifying a region of interest 32 in the subject. For example, the region of interest may be a portion of a blood vessel targeted for assessment of blood flow in the blood vessel. Once a region of interest is established, sampling site(s) for CT scan slices are identified 34 at or near the region of interest. Based on the predetermined sampling site(s), the subject is positioned 36 in the CT scanner in an alignment that allows for a radiation source of the CT scanner to direct radiation at the sampling site(s). Prior to scanning, the subject optionally holds breath 38 and maintains a breath-hold throughout scanning. As a further option, a hyperemic condition can be induced in the subject, for example by administering a vasodilator to the subject.

Figure 4:
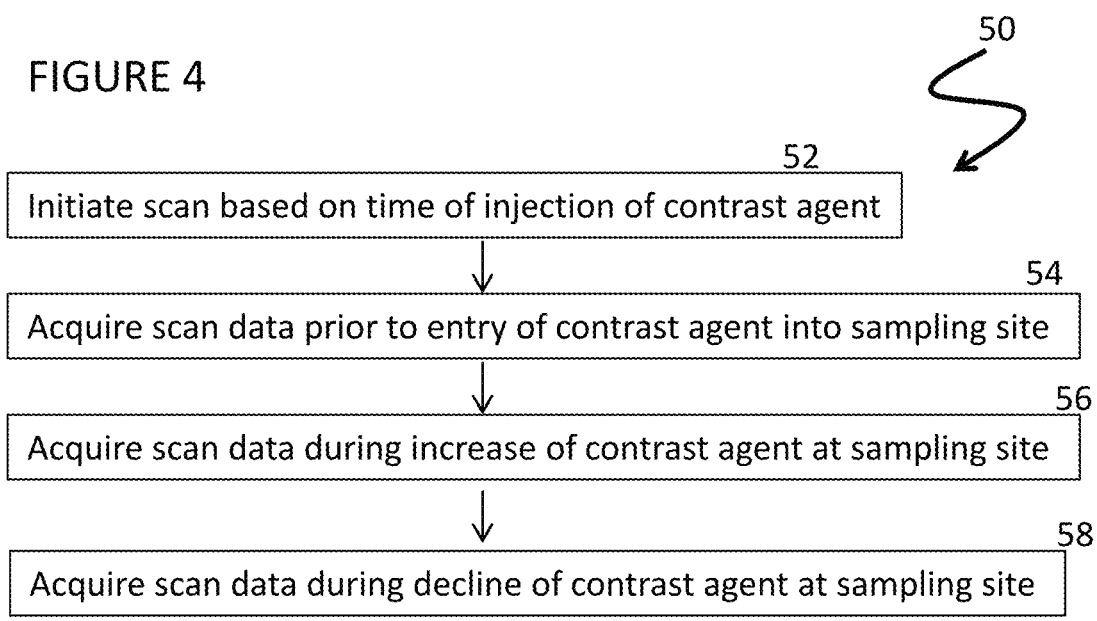
FIG. 4 shows a flow diagram of scan data acquisition in the imaging method shown in FIG. 2.

FIG. 4 shows an example of CT scanning 50 synchronized to injection of the contrast agent. The synchronized CT scanning 50 includes initiating a dynamic CT scan at a desired time based on an injection of the contrast agent. Optionally, the CT scanning can be synchronized to an electrocardiogram (ECG), such as provided by prospectively electrocardiogram (ECG) gated contrast-enhanced dynamic CT imaging. When ECG gating is deployed retrospective ECG-gating or prospective ECG-gating may be used. The dynamic CT scan includes acquiring of projection data prior to entry 54 of contrast agent at the sampling site(s) to set a baseline, as well as acquiring projection data during an increase phase 56 of the contrast agent at the sampling site(s) and acquiring projection data during a decline phase 58 of the contrast agent at the sampling site. An increase phase refers to an increase of mass of contrast agent at the sampling site as time advances subsequent to initial entry of the contrast agent into the sampling site, while a decline phase or decrease phase refers to a decrease of mass of contrast agent at the sampling site as time advances prior to substantially complete clearance of the contrast agent from the sampling site. Peak (maximum value) mass of contrast agent at the sampling site occurs during progression from the increase phase to the decline phase. Time elapsed from entry to clearance of contrast agent at the sampling site may be referred to as a transit time of the contrast agent. The duration of CT scanning is not limited by a requirement to capture a complete transit time of contrast agent at the sampling site provided that at least a portion of both increase and decrease phases are captured.

Figure 5:
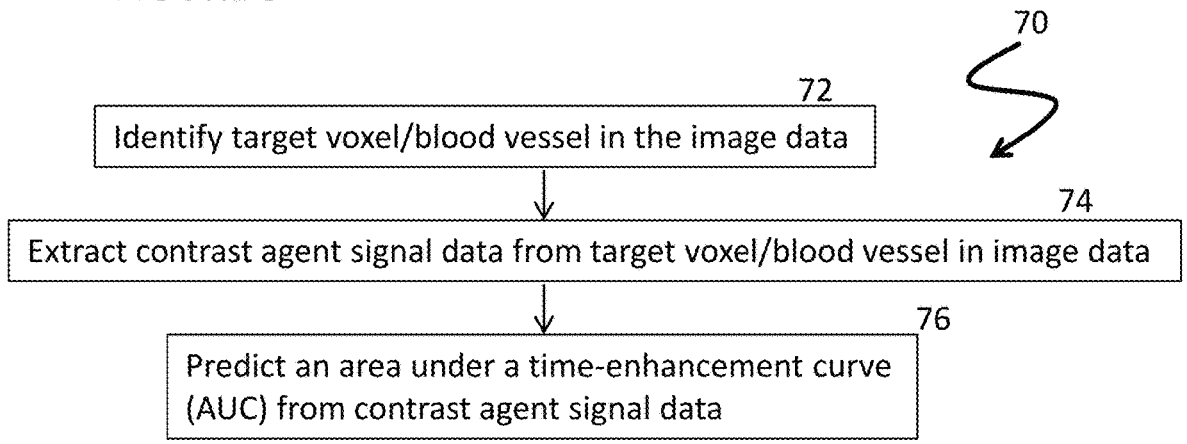
FIG. 5 shows a flow diagram of an example of predicting an area under time-enhancement curve (AUC) in the imaging method shown in FIG. 2.

FIG. 5 shows an example of image analysis to predict 70 an area under a time-enhancement curve with a machine learning model. Prediction of an area under a time-enhancement curve can include identifying 72 a voxel or region of interest within a plurality of corresponding images at the sampling site. Contrast agent signal data is extracted 74, for example contrast agent signal intensity, from an area defined by the voxel or region of interest from each of the plurality of corresponding images. An area under a time-enhancement curve is predicted by a computer-implemented learning model 74 based on the contrast agent signal data during the increase phase, the decrease phase, or both the increase phase and the decrease phase at the sampling site.

Figure 6A:
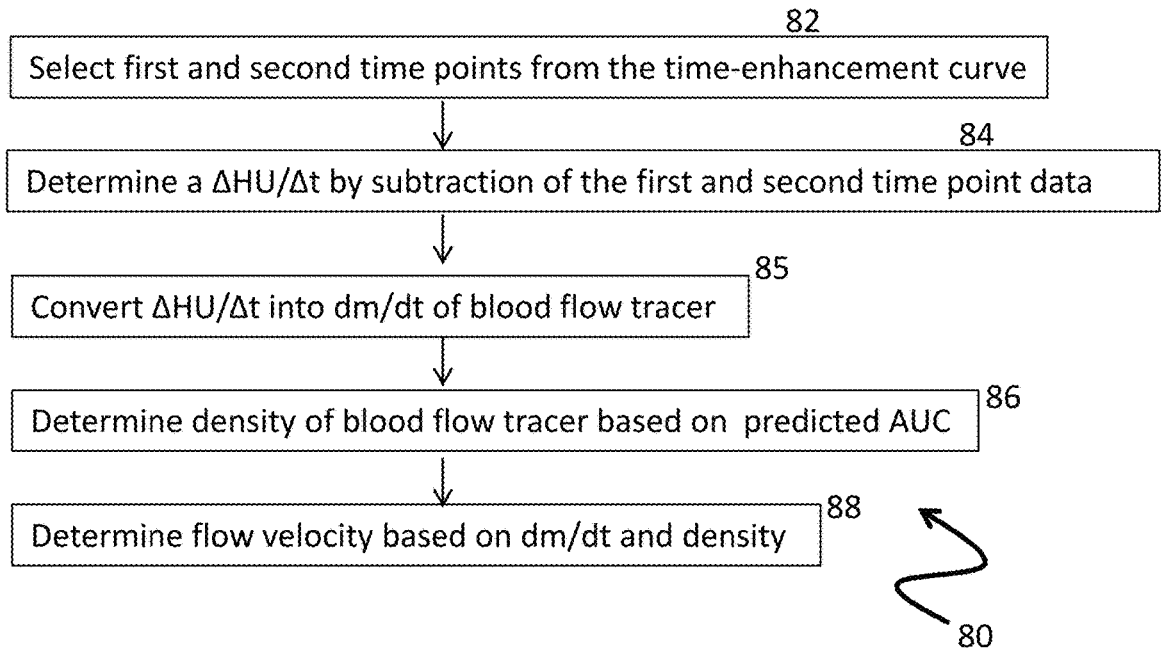
FIG. 6A shows a flow diagram of an example of determining a blood flow characteristic based on the predicted AUC in the imaging method shown in FIG. 2.

FIG. 6A shows an example of estimating blood flow 80 in a voxel or region of interest based on the time-enhancement curve. The estimation of blood flow can be achieved by determining a flow velocity value based on the time-enhancement curve. The determination of a flow velocity value can include selecting first and second time points 82 from the time-enhancement curve. A rate of change of enhancement ($\Delta HU/\Delta t$) 84 can be determined by subtraction of the CT image data at the selected first and second time points. Calculating a rate of change of tracer mass (dm/dt) 85 based on the rate of change of enhancement ($\Delta HU/\Delta t$) and the fractional volume of tracer solution that passes through the target voxel per unit time, for example using Equation 17 presented in co-owned PCT/CA2021/051189 filed 26 Aug. 2021. The tracer density can be determined 86 from the predicted area under the time-enhancement curve from step 76, for example using Equations 13, 14 and 15 presented in co-owned PCT/CA2021/051189 filed 26 Aug. 2021. Flow velocity through the target voxel is determined 88 based on the rate of change of tracer mass (dm/dt) and tracer density (p), for example using Equation 11B presented in co-owned PCT/CA2021/051189 filed 26 Aug. 2021. The determined flow velocity value can be communicated or displayed to a technician/operator or other end-user through any conventional computer or display device.

Figure 6B:
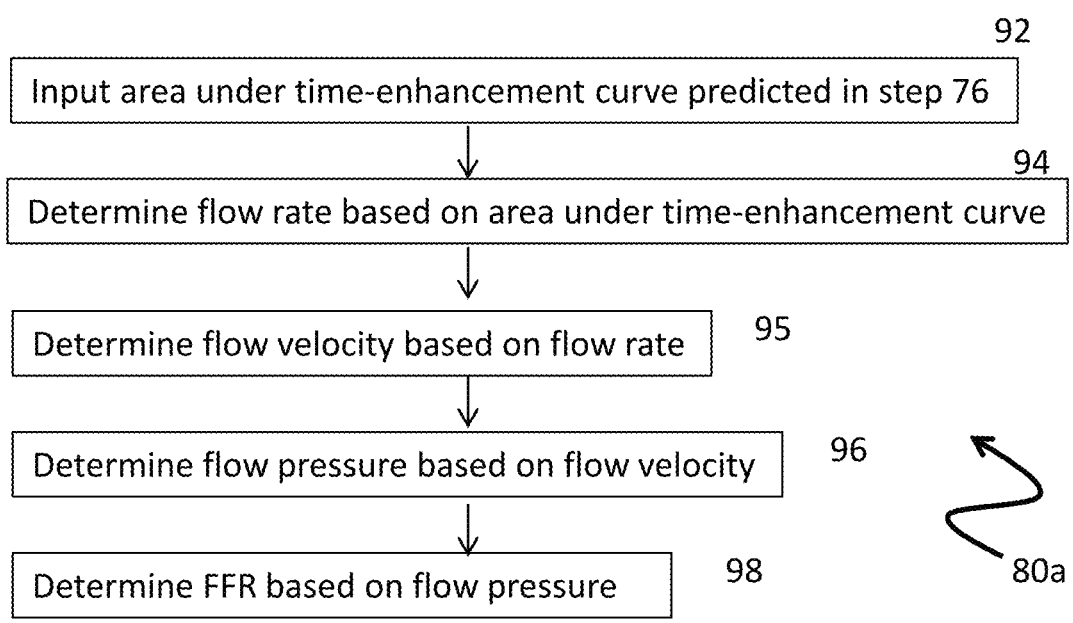
FIG. 6B shows a flow diagram of another example of determining a blood flow characteristic based on the predicted AUC in the imaging method shown in FIG. 2.

FIG. 6B shows another example (alternative to the example shown in FIG. 6A) of estimating blood flow 80a in a blood vessel of interest based on the time-enhancement curve. The estimation of blood flow 80a can be achieved by determining a fractional flow reserve (FFR) value based on the time-enhancement curve. The determination of an FFR value can include input 92 of the predicted area under the time-enhancement curve (AUC) from step 76. A flow rate 94 can be determined based on the predicted area under the time-enhancement curve, for example using an indicator-dilution principle as expressed in Equation 1 presented in co-owned PCT/CA2019/050668 filed 16 May 2019. A flow velocity can be determined 95 based on the flow rate and a calculated cross-section area of a lumen of the blood vessel at the sampling site, for example using Equation 2 presented in co-owned PCT/CA2019/050668 filed 16 May 2019. A flow pressure 96 can be determined from the flow velocity, for example using Bernoulli's equation as expressed in Equations 3A or 3B presented in co-owned PCT/CA2019/050668 filed 16 May 2019. Based on flow pressure 96 determined from at least two sampling sites a pressure gradient can be calculated, and an FFR value can be determined based on the calculated pressure gradient and a systolic blood pressure value, for example using Equation 11 presented in co-owned PCT/CA2019/050668 filed 16 May 2019. The determined FFR value can be communicated or displayed to a technician/operator or other end-user through any conventional computer or display device.

The blood flow imaging system and method have been mathematically validated. Mathematical analysis described in co-owned PCT/CA2019/050668 filed 16 May 2019 or in co-owned PCT/CA2021/051189 filed 26 Aug. 2021 show numerous examples of deriving blood flow characteristics from a dynamic contrast-enhanced dynamic CT imaging session that can all be incorporated within the current disclosure.

Figure 7A:
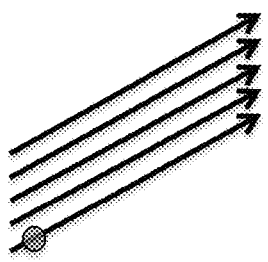
FIG. 7A and FIG. 7B show schematic illustrations of two approaches for studying the movement of fluid.
Figure 7A:
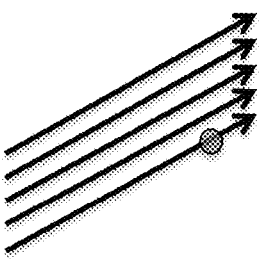
Figure 7B:
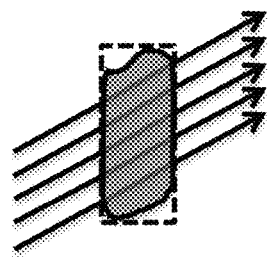
Figure 7B:
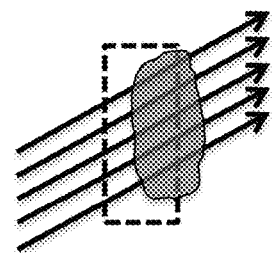

Fluid motion can typically be assessed by two approaches. The first approach is by monitoring the movement of individual particles in the fluid over time (FIG. 7A). Navier-Stokes Equations (derived from Newton's Second Law) can be used to describe the movement of any individual particle in the fluid in any direction. The second approach is by monitoring the passage of a small fraction of fluid within a fixed region (volume) over time (FIG. 7B). The monitoring region or frame of reference (rectangle outlined with dark dashed line in FIG. 7B) does not move over time. The small fraction of fluid contains many individual particles that cannot be resolved, but this second approach is computationally less intensive compared to the first approach, and the results give a good approximation of the fluid movement with a reasonably good spatial resolution. Without wishing to be bound by theory, the second approach provides the basis of the analytic imaging method disclosed herein.

Figure 8A:
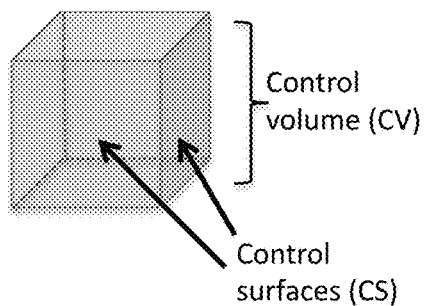
FIGS. 8A and 8B show schematic representations of voxel-defined control volume analysis of flow imaging data.

In CT, an image voxel, or a block of image voxels, is selected as the fixed region to monitor the movement of fluid (e.g. blood) over time. This frame of reference is called a control volume and the surface on each side of the control volume is called a control surface (as illustrated in FIG. 8A). Fluid can move in and out of the control surface in any direction.

Figure 8B:
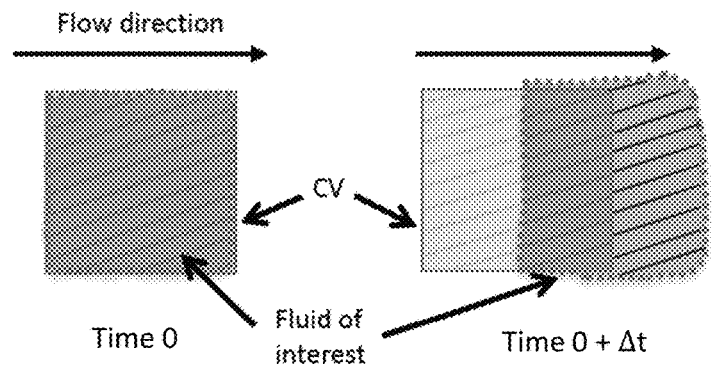

For illustration, an example shown in FIG. 8B depicts movement of a small amount of fluid (grey region outlined with a dashed grey line) with respect to a control volume (CV). Here, the CV is shown in a two-dimensional view. At time 0, the fluid of interest (the grey region marked with mid-grey stripes) fills the CV completely. At a later time (time 0+$\Delta t$), the same fluid of interest starts to move out of the CV in the flow direction shown in FIG. 8B. The dark-grey stripes denote the portion (mass) of fluid that leaves the CV at time 0+$\Delta t$ and the vacant space within the CV is filled by the incoming fluid (marked with light-grey stripes). The mid-grey stripes represent the portion of fluid that remains in the CV at time 0+$\Delta t$. If the mass of incoming fluid that fills the vacant space of CV equals the mass of fluid that leaves the CV, then the flow condition is considered as steady. If the two masses (light-grey and dark-grey portions) are not equal to each other, then the flow is considered as unsteady. It should be noted that unsteady implies the flow is either turbulent, or in the transition between the steady and turbulent states. At any time, the total mass of the fluid of interest (the fluid region delineated by the dashed grey line in FIG. 8B) is unchanged. That is, the mass in the area marked with the mid-grey stripes at time 0 should equal the total mass in the area marked with the mid-grey and dark-grey stripes at time 0+$\Delta t$. The movement of fluid with respect to a CV can be described using the Reynolds Transport Theorem.

Figure 9A:
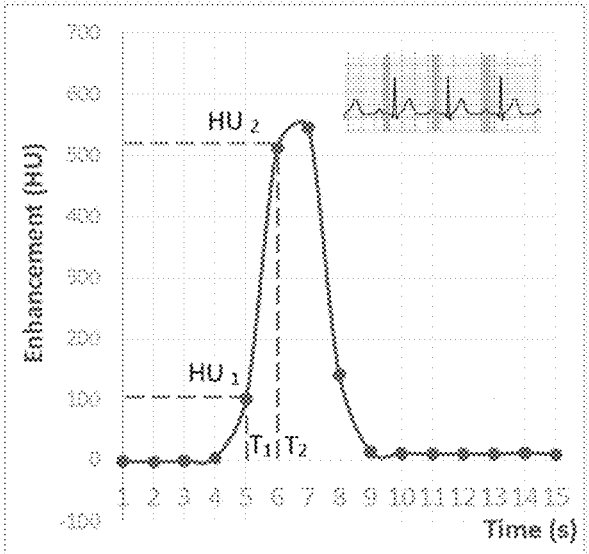
FIGS. 9A and 9B shows schematic illustration for two different approaches of dynamic image acquisition and reconstruction for obtaining AHU/At that is a basis for absolute or relative flow velocity assessment.
Figure 9B:
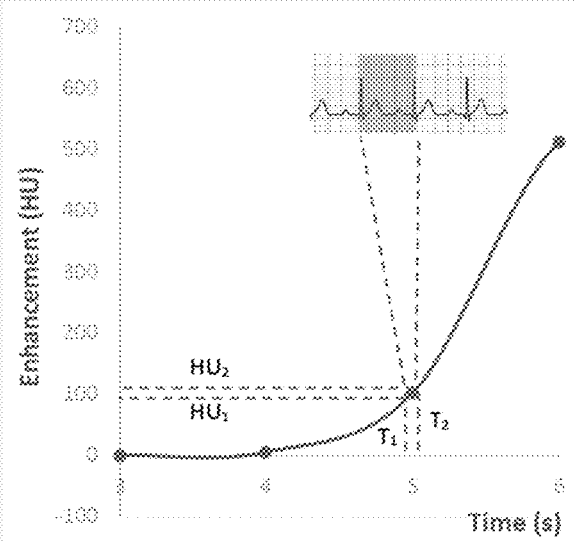

FIGS. 9A and 9B shows schematic illustration for two different approaches of dynamic image acquisition and reconstruction that is a basis for absolute or relative flow velocity assessment. FIG. 9A shows image acquisition and reconstruction at the same cardiac phase (e.g. 75% R-R interval or diastole) over multiple time points. FIG. 9B shows image acquisition covering a full cardiac cycle (systole and diastole); multiple image sets corresponding to different cardiac phases are reconstructed.

The blood flow imaging technology described herein uses supervised machine learning (ML) or supervised deep learning (DL) algorithm to simplify the clinical workflow for functional assessment in vascular diseases with CT. Herein, we use the cardiac application for illustration but the blood low imaging technology can be applied to other vascular diseases as well.

In a routine cardiac CT test, coronary CT angiography (CCTA) is acquired first to determine if a patient has any obstructive stenosis in a coronary artery. Prior to the CCTA scan, a bolus tracking (BT) scan is initiated to determine the optimal acquisition time for the CCTA scan. A BT scan is a real-time tracking technique in which the signal intensity or enhancement in a region of interest (ROI) is monitored at consecutive time points following an intravenous bolus injection of contrast solution into the patient. When the signal intensity in that monitoring ROI reaches a pre-defined threshold value, the CCTA scan is automatically executed at a delayed time (approximately 5 to 7 seconds) to ensure the CCTA scan captures the peak or near peak contrast enhancement in the coronary arteries. Alternatively, a non real-time tracking timing bolus (TB) scan can be used instead of a real-time tracking BT scan for estimating the peak enhancement time in the artery of interest. A TB scan is similar to a dynamic perfusion scan, with the exception that the volume and iodine concentration of contrast solution injected for the TB scan are usually less compared to those used in a CCTA scan or perfusion scan. Furthermore, a TB scan is set up as an independent series from a CCTA scan. While a BT scan is used for illustration of an ML/DL implementation, it will be understood that the same concept can be easily extended with a TB scan used instead of a BT scan.

In a typical clinical workflow, if there is absence of obstructive stenosis in the CCTA images, no further functional assessment is required. If the CCTA scan confirms the presence of obstructive stenosis, particularly if the degree of the stenosis is between 40 to 90% in lumen diameter, then a dynamic perfusion scan can be acquired during maximal vasodilation for functional evaluation of the stenosis (i.e. to determine if the stenosis is flow-limiting). In some situations, a dynamic perfusion scan is also acquired at rest to determine the magnitude of blood flow increase from baseline for a more accurate functional assessment.

Figure 10:
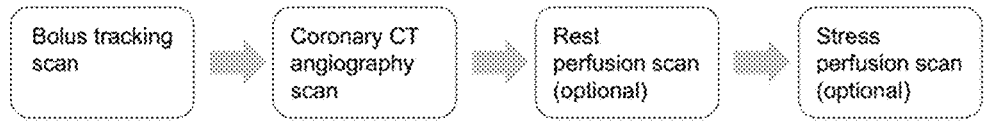
FIG. 10 shows a schematic illustration of an example of workflow of a cardiac CT test.

Thus, as summarized in FIG. 10, in examples of clinical workflow progression of a cardiac CT test, the BT and CCTA scans are typically performed in a cardiac CT test while the perfusion scans are optional (depending on the CCTA findings). Both the BT and CCTA scans are performed in the resting condition.

Figure 11:
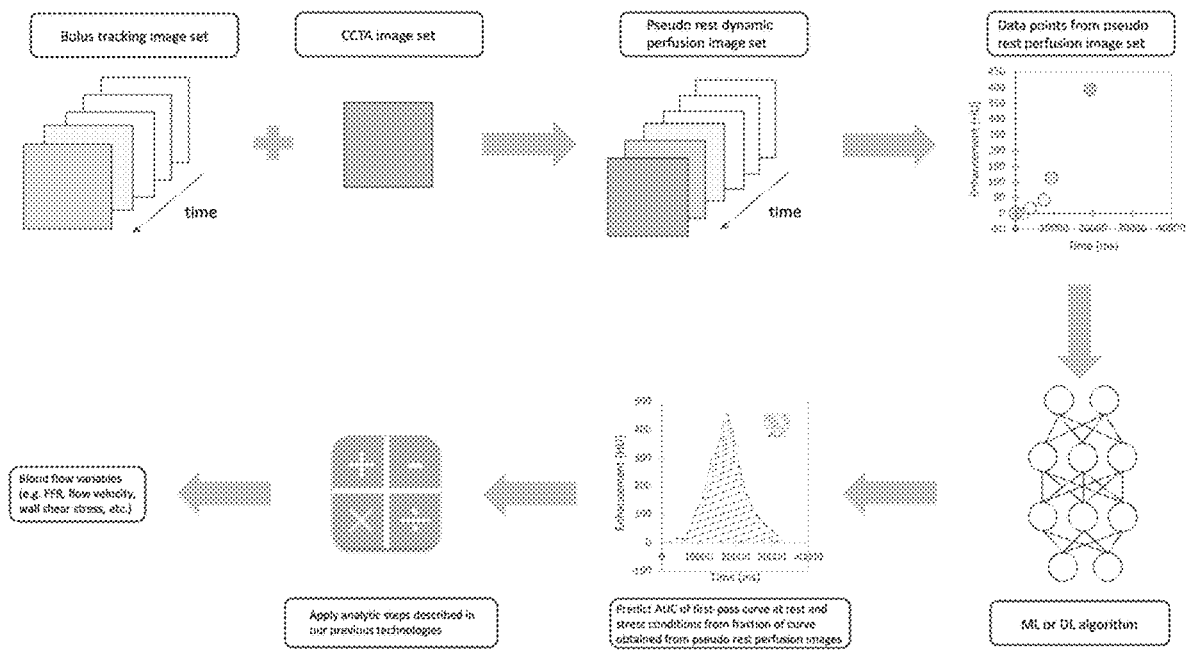
FIG. 11 shows a schematic illustration of an example of using machine learning or deep learning to derive blood flow variables from a pseudo truncated dynamic perfusion scan.

FIG. 11 shows a schematic of an example of blood flow imaging incorporating a machine learning model:
1. combine the BT scan and CCTA scan as a pseudo truncated dynamic perfusion scan.
2. track the temporal changes of enhancement in each coronary artery from the pseudo truncated dynamic perfusion scan.
3. use ML or DL to predict the area under the time-enhancement curve in a coronary artery during the whole first-pass phase based on the findings in (2).
4. use ML or DL to predict the area under the time-enhancement curve in a coronary artery during maximal vasodilation (hyperemia) from the AUC predicted in (3).
5. use the AUC predicted in (4) coupled with the analytic algorithms disclosed in our previous technologies to derive blood flow variables such as fractional flow reserve (FFR).

Figure 12:
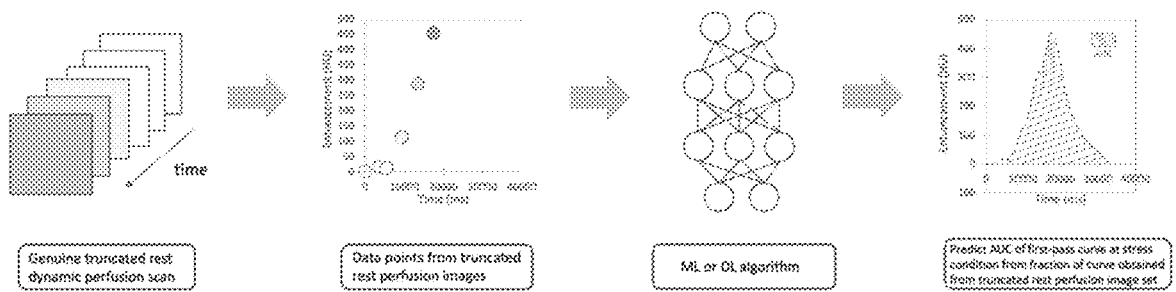
FIG. 12 shows a schematic illustration of an example of using machine learning or deep learning to derive blood flow variables from truncated rest dynamic perfusion scan.
Figure 13:
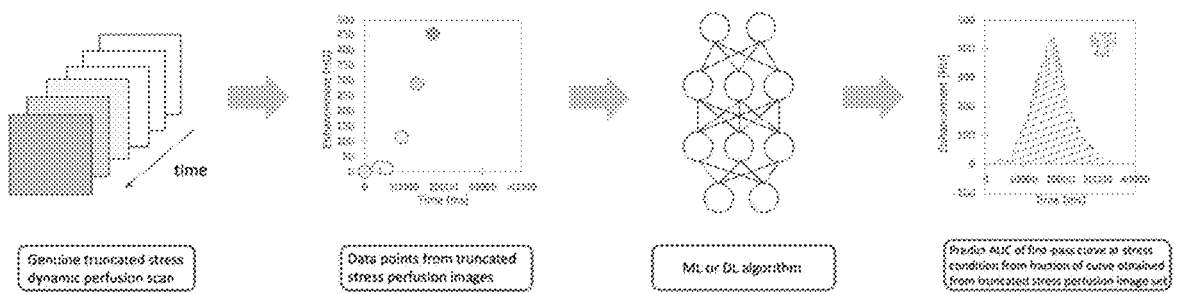
FIG. 13 shows a schematic illustration of an example of using machine learning or deep learning to derive blood flow variables from truncated stress dynamic perfusion scan.

A similar approach can be applied in other scenarios. More specifically, one example is the application of ML or DL to predict the area under a full coronary time-enhancement curve from a genuine truncated dynamic rest perfusion scan covering 5 or more time points (FIG. 12). Another example is the application of ML or DL to predict the area under a full coronary time-enhancement curve from a genuine truncated dynamic stress perfusion scan covering 5 or more time points (FIG. 13). Moreover, ML or DL can also be applied to predict the area under a time-enhancement curve at one location in a coronary artery in a short-axis plane from the time-enhancement curve sampled at the same location in a coronary artery in the axial plane.

Both ML and DL are artificial intelligence techniques that teach computers to learn from training dataset in a way similar to how humans learn from past experiences. Furthermore, supervised ML and DL refer to the use of labeled training dataset for computer learning. A difference between ML and DL is that a ML algorithm requires human intervention (such as manual feature extraction) for computer learning, while a DL algorithm can automatically extract relevant features in the training dataset without human intervention. Contrasting ML and DL is for convenience of discussing the segmentation task as DL is advantageous for the segmentation task, while both ML and DL can perform the AUC prediction task.

DL is subset of ML, and therefore the term ML encompasses DL, and where ML and DL is contrasted it is intended to contrast non-deep learning to DL approaches, and not to suggest that ML and DL are mutually exclusive categories of computer learning models.

Figure 14:
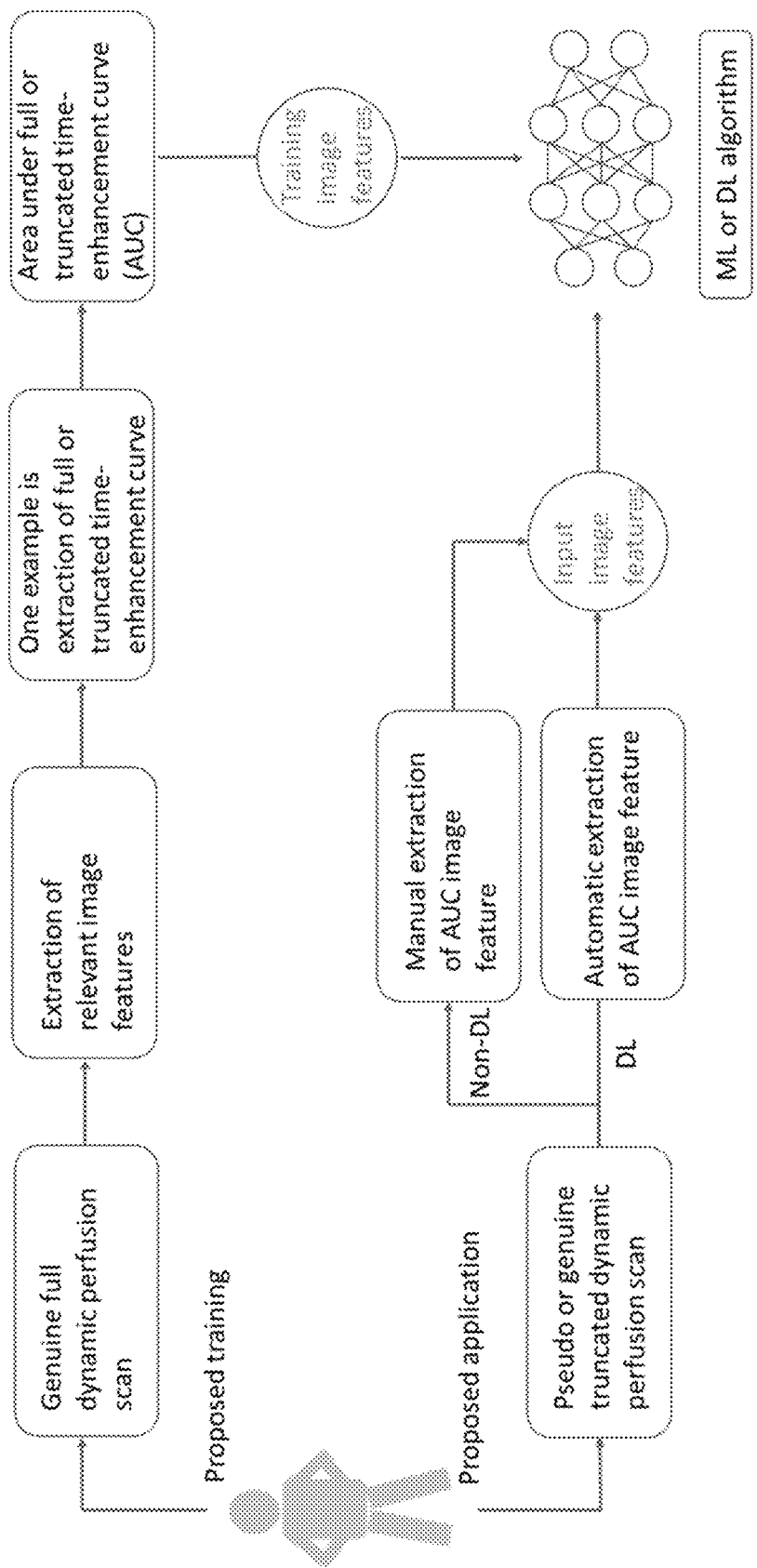
FIG. 14 shows a schematic illustration of an example of generation of training image features for training a ML or DL algorithm to learn from and make prediction on the AUC values for future truncated perfusion image data. Top: training path. Bottom: application path.

Machine Learning Approach. In an example of a ML approach, the computer is trained to develop a regression model that predicts the area under a full coronary time-enhancement curve by learning from some labeled images provided to the computer. The training image set comes from either a pseudo or genuine truncated dynamic perfusion scan. The training images are assigned with labels corresponding to the AUC values of full coronary time-enhancement curves. The labels (ground truth) are derived from a genuine full dynamic perfusion scan acquired from the same patient. The features where the computer can learn from can be image based or non-image based or both (FIG. 14).

Image-based features may include but are not limited to the following variables: enhancement (pixel signal intensity) in coronary arterial lumen, thickness of myocardial wall surrounding the left ventricle, size of left atrium, size of left ventricle, diameter of coronary artery, morphology of coronary artery, degree of stenosis in coronary artery, etc.

Non-image based features may include but are not limited to the following variables: patient's age, sex, weight, heart rate, blood pressure, x-ray tube voltage, x-ray tube current, contrast-injection rate, iodine concentration in contrast solution, etc.

Figure 15:
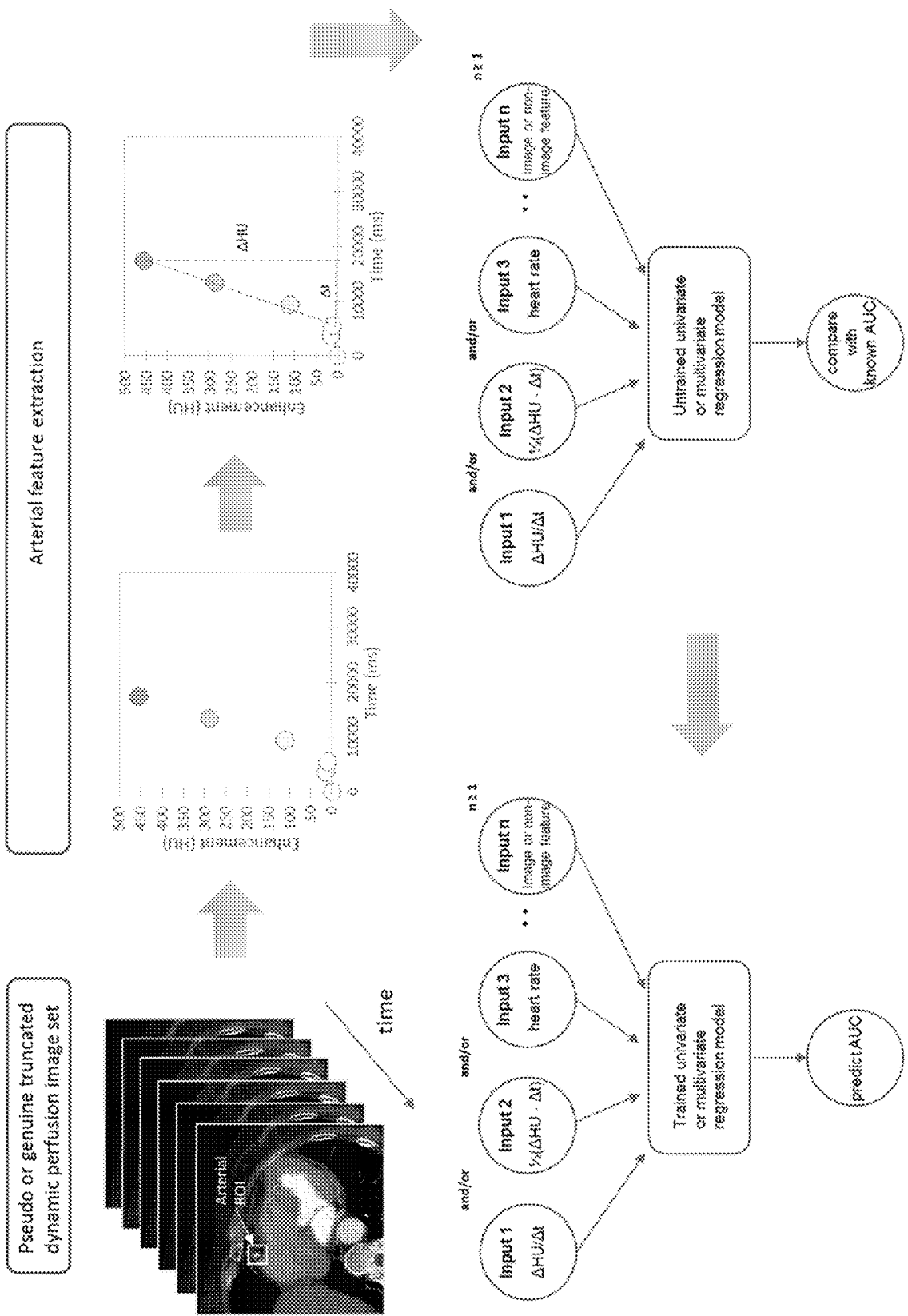
FIG. 15 shows a schematic illustration of an example of extraction of image features with optional incorporation of non-image features in a coronary artery for training a ML or DL algorithm.
Figure 16:
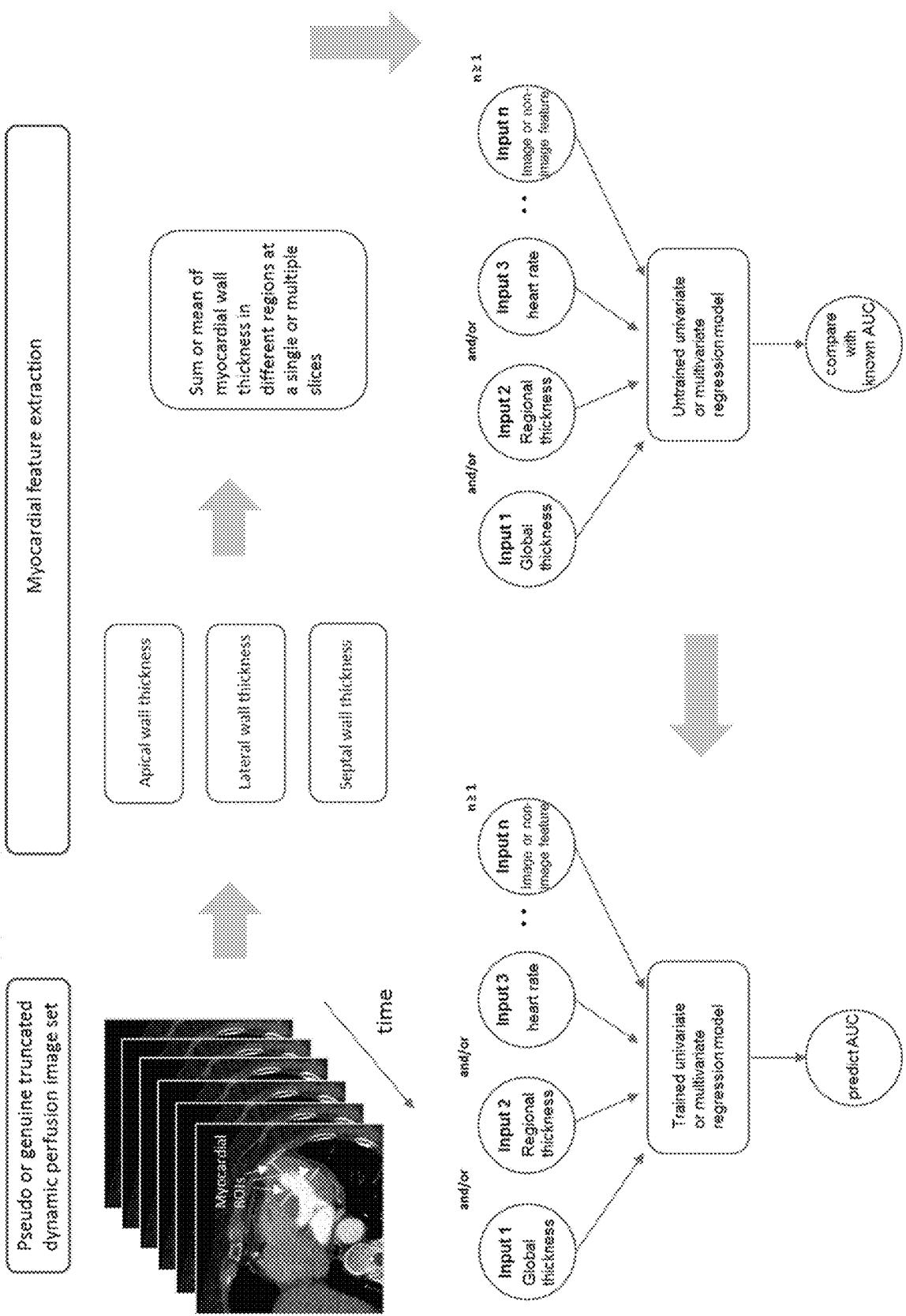
FIG. 16 shows a schematic illustration of an example of extraction of image features with optional incorporation of non-image features in the myocardium for training a ML or DL algorithm.

FIG. 15 and FIG. 16 provide schematic illustrations on how different image-based features can be used to train a ML algorithm to make predictions about the AUC values.

In the first illustration, the coronary enhancement at different time points can be combined into a single image-based feature with one of the following ways (FIG. 15):
1. The difference in Hounsfield Unit (HU, unit of CT image pixel value) between any two time points in the non-baseline (enhanced) phase.
2. The difference in HU between any two time points in the non-baseline phase divided by the time difference between the two selected time points.
3. The area under the truncated time-enhancement curve between any two time points in the non-baseline phase.

4. Any of the #1 to #3 with unit conversion from HU to iodine concentration (in milligram per mL).

In the second illustration, the myocardial wall thickness in different regions can be used individually or collectively as input feature(s) for training the ML algorithm (FIG. 16). Furthermore, as illustrated in FIGS. 6 and 7, image and non-image features can be used conjunctionally as the input features for the training. The computer will determine which of the input features have the highest correlation with the labelled feature (AUC values) and keep them in the regression model for future prediction on the AUC values.

Deep Learning Approach. Unlike the ML approach, the DL approach can rely on a deep artificial neural network to recognize relevant image features by itself.

Figure 17:
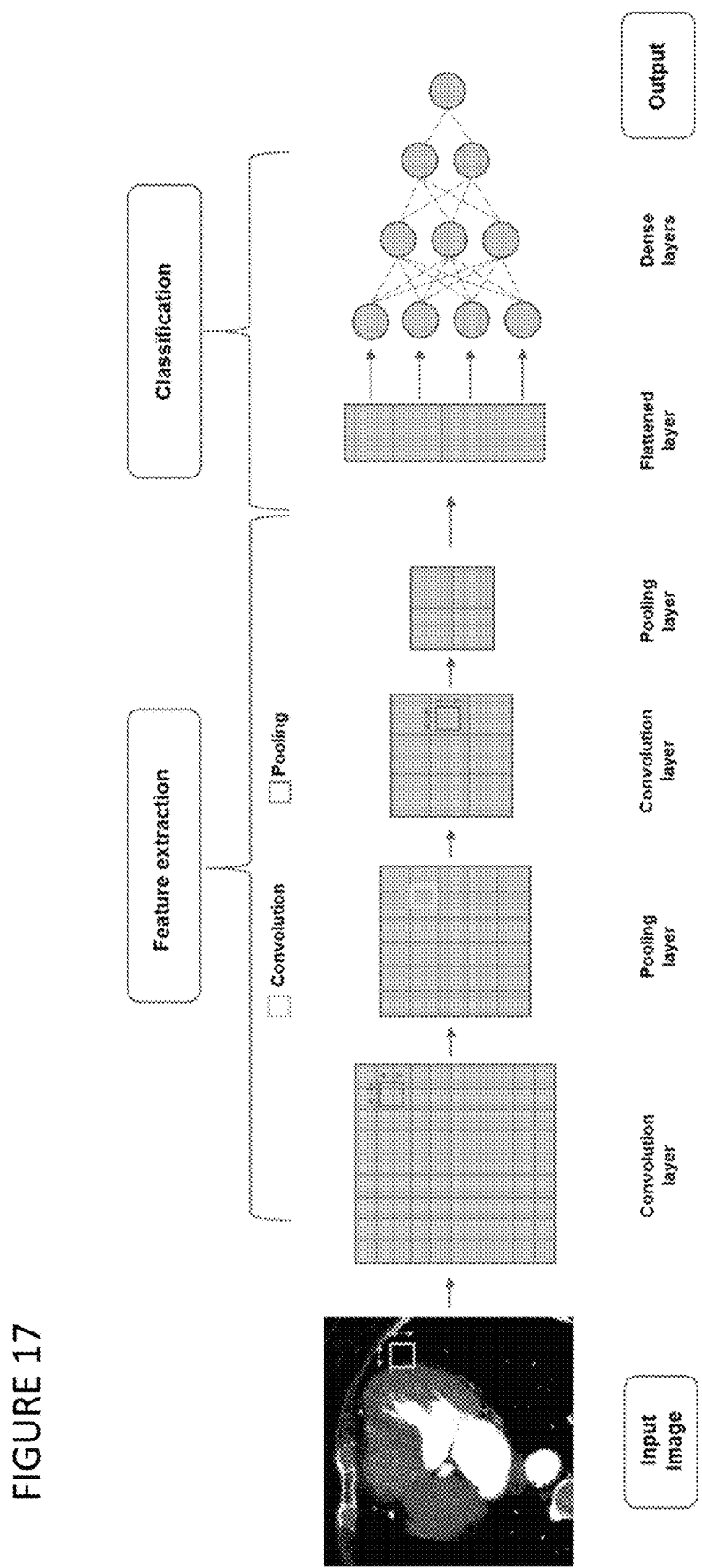
FIG. 17 shows a simplified diagram to illustrate an example of architecture of a deep neural network (convolution neural network). In this illustration, only one convolution filter is shown, resulting in only one feature map and pooled feature map from each round of convolution and pooling. The grids in each feature map and pooled feature map do not represent the actual dimensions in these maps, and only serve to demonstrate reduced dimensions in these maps after each operation. If an input image has M×M pixels and a convolution filter has C×C pixels, the feature map should have (M−C+1)×(M−C+1) pixels.

As illustrated in FIG. 17, a basic artificial neural network consists of three layers: an input layer, a hidden layer and an output layer. A "deep" artificial neural network is the network with more than one hidden layer. Many hidden layers are needed to accomplish a more sophisticated task, which is the case for our application. The input layer is where the input values are accepted by the network, and the output layer is where the final prediction is made. In between, the hidden layers take the input values and perform some computations based on the input variables. The results generated by the hidden layers are propagated to the output layer where the final prediction is made (i.e. regression for the current example).

In one example, the hidden layers consist of: multiple convolution layers, multiple pooling layers, a flattened layer, multiple dense layers (or fully connected layers).

A CT image has 512×512=262144 pixels. For any grey-scale image like a CT image, every pixel in the image has a value ranging from 0 to 255. Conventionally, a darker pixel has a lower value and a brighter pixel has a higher value. A CT image is not directly passed to the dense layers. Instead, a mathematical operation called convolution is used to extract only the desired information from the image as the inputs for the dense layers. During the convolution process, multiple filters are overlayed to a two-dimensional CT image and sliced through the image (from top left to bottom right). Each filter is a mathematical matrix with a small dimension such as 3×3 or 5×5 pixels. The extracted image information from the convolution with each filter is passed through an activation function and the results are stored in a new matrix with a reduced dimension (also called a feature map). Afterwards, a pooling filter (usual dimension is 2×2 pixels) is applied to the feature map for reducing the dimension of the feature map while preserving the most distinguished information. A pooled feature map is generated as a result. This image processing sequence (convolution→activation→pooling) can be repeated for several times and the dimension of the feature and pooled feature maps are reduced after each iteration. After the final iteration, the pooled maps are converted to a one-dimensional vector (flattened layer) as the inputs for the dense layers.

Figure 18:
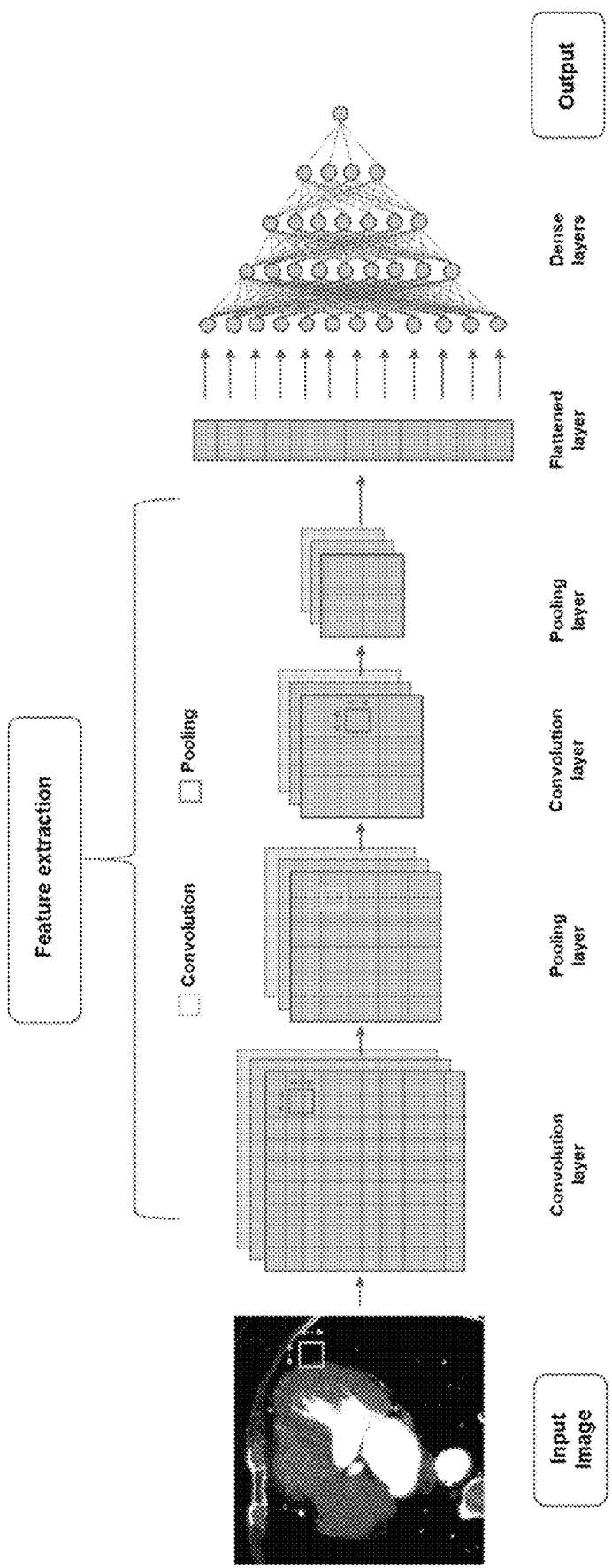
FIG. 18 shows an example of an analog of the deep neural network shown in FIG. 17, but with three convolution filters applied.

Each convolution filter is designed for a specific pattern recognition, and as such, many filters are needed for more complicated image patterns. The number of feature map generated after a convolution is the same as the number of convolution filter applied (FIG. 18).

Each dense layer has many interconnected nodes called neurons. At each neuron, each input variable is multiplied by a weight (a bias may also be added) before undergoing a non-linear transformation by passing through an activation function. The purpose of this computation is to determine whether a specific input variable should be passed to the next layer.

Figure 19:
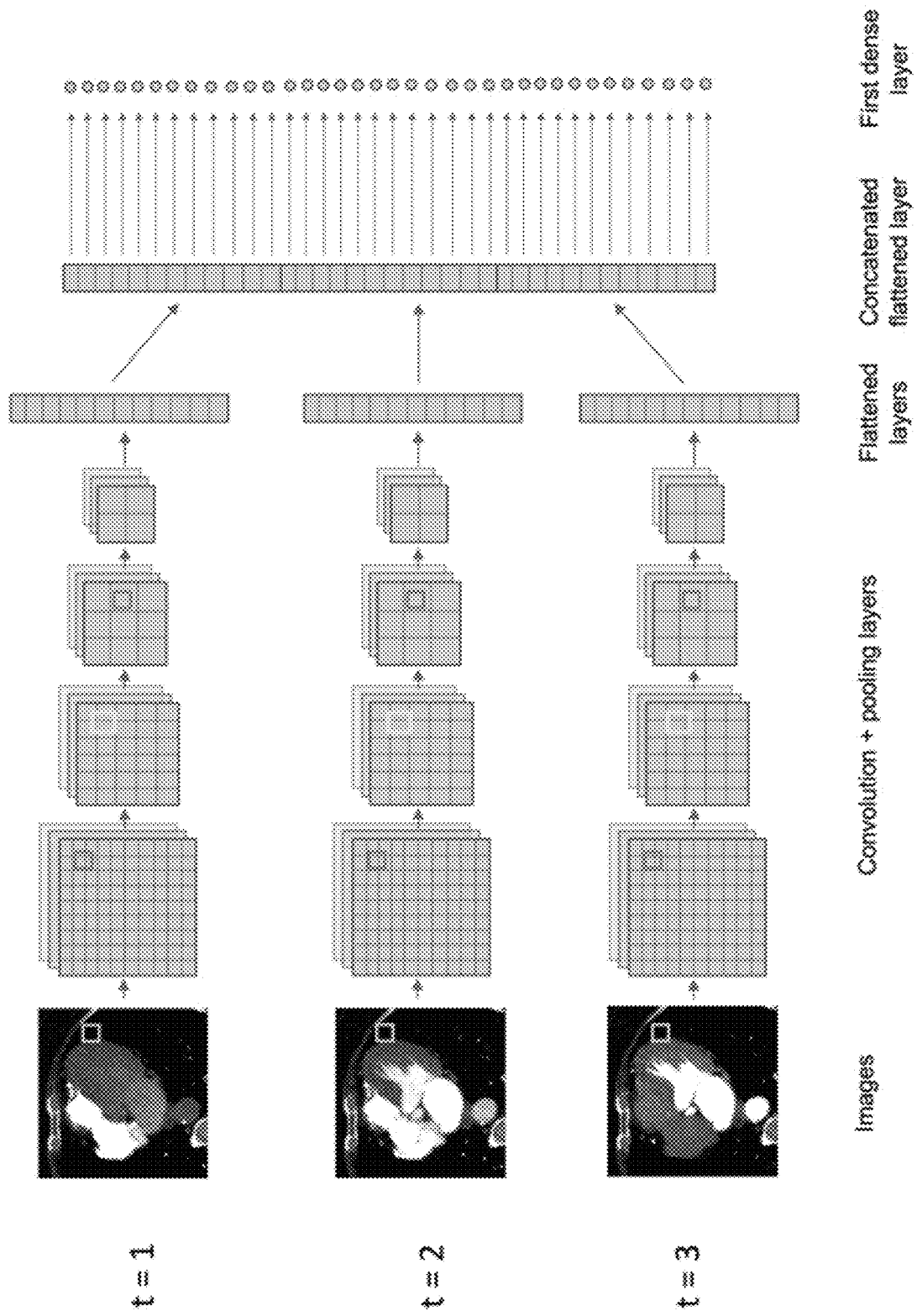
FIG. 19 shows a schematic illustration of an example of deep neural network architecture for handling a dynamic perfusion image set. For visual simplification, only a portion of the architecture is shown.

A dynamic image set can be handled by a DL algorithm in the following way: First, generate multiple inputs with a convolution stack for each image corresponding to a specific time point. Second, apply concatenation to the flattened layer corresponding to each time point to aggregate the temporal information from all the images in a dynamic series. Last, the concatenation flattened layer provides the inputs to the first dense layer (FIG. 19).

In summary, both ML and DL methods can predict the AUC of a truncated time-enhancement curve from the image features presented in the dynamic perfusion images (non-image features may also be used), but can differ in input features. When a trained ML algorithm is used, the user will need to provide the input features with aids of image processing tools in the software. For instance, place a sampling ROI in the pseudo or genuine dynamic image set to obtain a truncated time-enhancement curve, or place a measuring tool across the myocardium to measure the wall thickness. The ML algorithm will then take the input features and make prediction on the AUC values, from which blood flow variables such as FFR can be computed with the analytic steps disclosed in our previous technologies. On the other hand, when a trained DL algorithm is used, the user only needs to load the dynamic image set and the algorithm will automatically identify the relevant input features and predict the AUC values and subsequently the blood flow variables.

The blood flow imaging system and method have been validated by experimental testing. Experimental testing results demonstrate the ability of the blood flow imaging system and method to determine one or more of several blood flow characteristics. The following experimental examples are for illustration purposes only and are not intended to be a limiting description.

Experimental Exemplification: Experimental Example 1 (Relationship Between AUC and Degree of Lumen Narrowing)

Figure 20A:
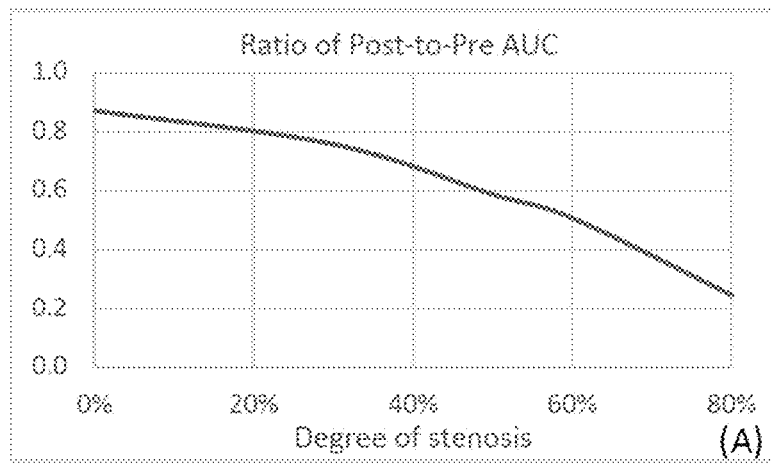
FIG. 20A shows post-stenotic AUC normalized to pre-stenotic AUC as a function of luminal narrowing in five patients with coronary artery disease (CAD).
Figure 20B:
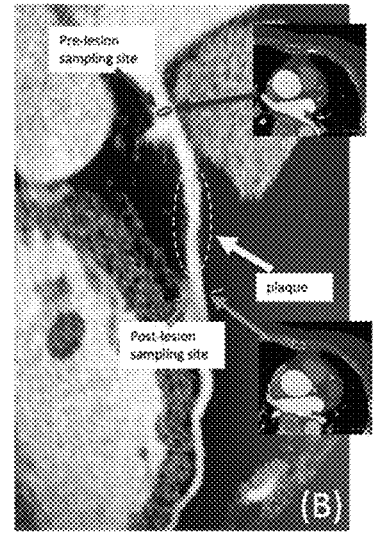
FIG. 20B shows sampling ROIs in the pre-stenotic and post-stenotic segments in a narrowed coronary artery.

As explained in co-owned PCT/CA2019/050668 filed 16 May 2019 or in co-owned PCT/CA2021/051189 filed 26 Aug. 2021, the volumetric flow rate, F (shown as Q in Equation 1), in a blood vessel can be estimated with the indicator-dilution principle:

$$Q = M_t / \int c(t) dt \qquad (1)$$

where m in Eq. (1) is the mass of tracer in the blood vessel, the integral in the denominator in the equation is the area under the time-enhancement curve (AUC). The integral in the denominator is the integral of tracer (interchangeably referred to as contrast agent) concentration as a function of time at a region of interest, and therefore AUC represents a total sum of tracer concentration time product at the region of interest. Since F and AUC are inversely proportional to each other, a smaller AUC reflects a higher volumetric flow rate. Our data shows a clear inverse non-linear relationship between the degree of stenosis in a coronary artery and the AUC of a coronary time-enhancement curve (FIG. 20).

Figure 21:
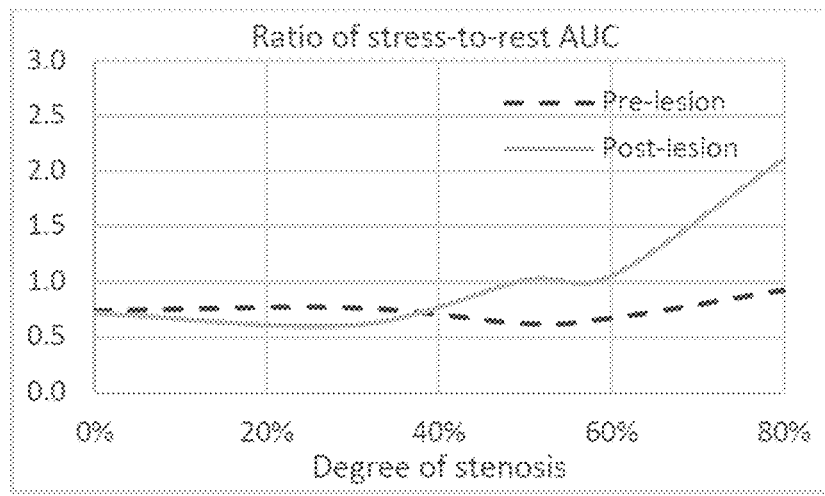
FIG. 21 shows stress AUC normalized to rest AUC in pre-stenotic and post-stenotic coronary segments in 5 patients with CAD.

In a stenosed coronary artery, the magnitude of increase in volumetric flow rate from baseline (rest condition) is attenuated in the post-stenotic coronary segment if the stenosis exceeds a certain degree (~40% luminal narrowing), and it is reflected by a larger ratio of the stress AUC to rest AUC in this segment compared to the pre-stenotic segment (FIG. 21). The graphs shown in FIG. 20 and FIG. 21 collectively indicate that the AUC of a coronary time-enhancement curve is predictable if other information such as the degree of coronary stenosis is known, which supports the notion of using ML or DL algorithms to learn and predict the AUC values.

Experimental Exemplification: Experimental Example 2 (Relationship Between Time-Enhancement Curve and Heart Rate)

Figure 22:
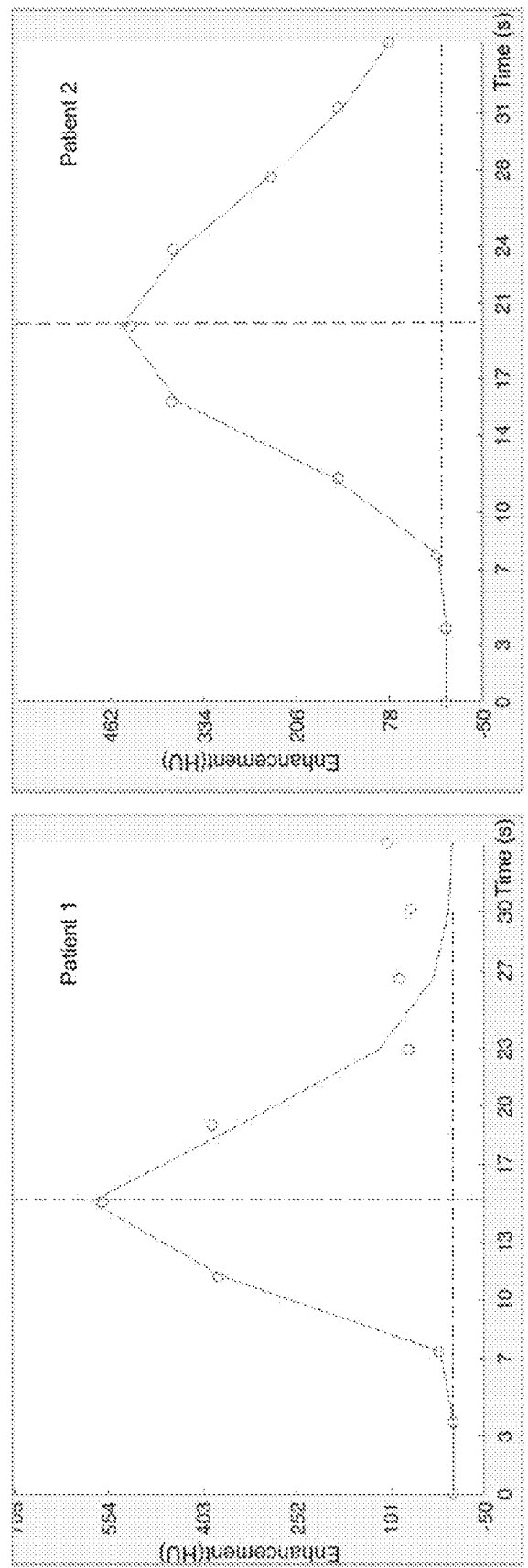
FIG. 22 shows coronary time-enhancement curves obtained in two different patients with different heart rates. Open circles are the original data and solid lines are the corresponding fitted curves. The projected baseline and peak enhancement of each fitted curve are denoted by the blue dashed horizontal and vertical lines, respectively.

Although the symmetry of a coronary time-enhancement curve following a bolus intravenous injection of contrast media is relatively unaffected by the patient's heart rate, the width of the curve may be partially dependent on the patient's heart rate (FIG. 22). This indicates that non-image feature such as patient's heart rate may also be a useful input variable for the ML or DL algorithms to make prediction on AUC.

Experimental Exemplification: Experimental Example 3 (Shape of Time-Enhancement Curve at Different Vascular Sizes)

FIG. 23 shows that the fitted time-enhancement curve obtained from the myocardium (after removing the contrast retention and recirculation effects) has a similar symmetry compared to the fitted time-enhancement curve obtained from the feeding epicardial coronary artery. This finding indicates that the proposed ML and DL methods can also be applied to estimate the first-pass time-enhancement curve at the microvascular level with either a pseudo or genuine truncated dynamic perfusion image set.

Experimental Exemplification: Experimental Example 4 (Relationship Between Myocardial Wall Thickness and Coronary Diameter and AUC)

Figure 24C:
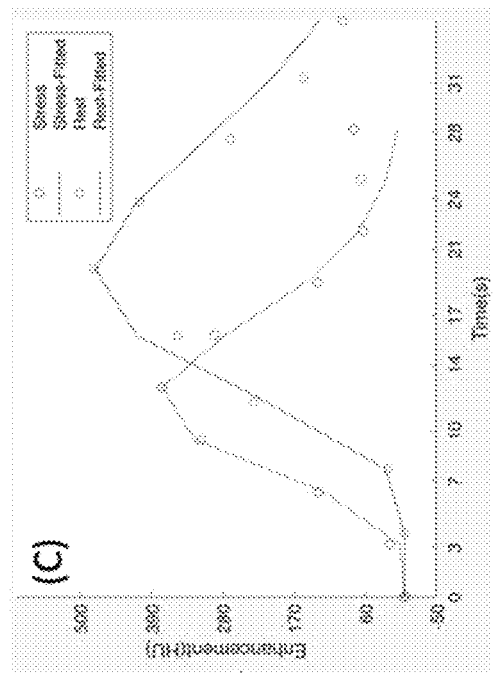
FIG. 24C shows the corresponding time-enhancement curves measured from the RCA at stress and rest.
Figure 24B:
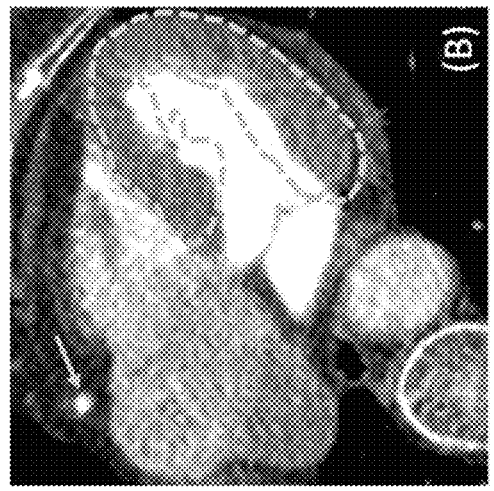
FIG. 24A and FIG. 24B show an increase of thickness of the myocardial wall (dotted lines) increases when comparing a maximal vasodilatory stress condition (FIG. 24A) to a resting condition (FIG. 24B). The right coronary artery (RCA; indicated by arrows) also appeared to be more dilated at stress.
Figure 24A:
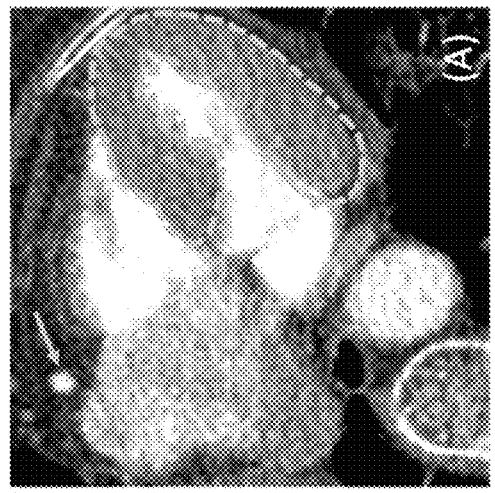

As discussed in Experimental Example 1, the AUC is different between the rest and stress (hyperemic) conditions. During maximal hyperemia arising from intravenous adenosine administration, the patient's cardiac contractility and coronary artery diameter may increase substantially compared to the baseline levels. Therefore, image features such as myocardial wall thickness and coronary diameter (or radius or circumference) may be used as the input variables for the ML or DL algorithm to predict AUC (FIG. 24).

Experimental Exemplification: Experimental Example 4 (Time-Enhancement Curves in Different Tomographic Views)

Figure 25A:
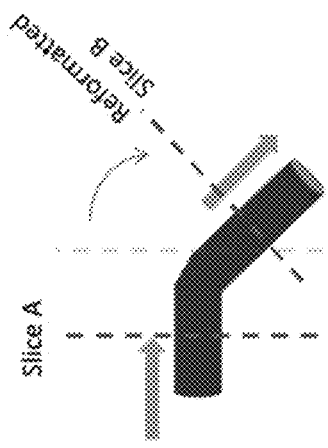
FIG. 25A shows a default orientation of two CT slices relative to a coronary artery. The red arrows depict the direction of blood flow in the artery.
Figure 25B:
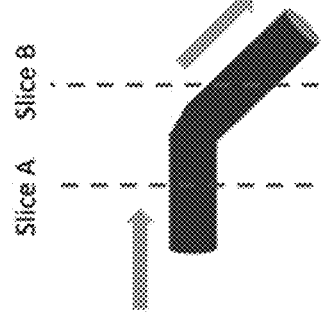
FIG. 25B shows slice reformation in one slice location is needed to ensure the slice is perpendicular to the direction of blood flow prior to quantitative blood flow assessment.

As explained in co-owned PCT/CA2019/050668 filed 16 May 2019 or in co-owned PCT/CA2021/051189 filed 26 Aug. 2021, the pressure gradient between two sampling slices A and B in a blood vessel can be estimated with the Bernoulli's equation:

$$P_A + \tfrac{1}{2}\rho V_A^2 + \rho g h_A = P_B + \tfrac{1}{2}\rho V_B^2 + \rho g h_B + P_L \qquad (2)$$

where $P_A$ and $P_B$ are the coronary flow pressure (in Pascal or Pa) in slice A and B respectively, $\rho$ is the density of blood (g/cm$^3$), g is the Earth's gravity (980 cm/s$^2$), $h_A$ and $h_B$ are the relative height (in cm) above or below a reference plane from the center point in slice A and B, $V_A$ and $V_B$ are the flow velocities at slice A and B respectively, and $P_L$ is the pressure (energy) loss due to friction and/or turbulence. $V_A$ and $V_B$ should be calculated from the time-enhancement curves sampled at the tomographic slices perpendicular to the direction of blood flow. Due to the nature of arterial curvature, the imaging slices are not always perpendicular to the direction of flow. In this case, the tomographic images should be reformatted into the desired view before sampling the time-enhancement curves for blood flow calculation (FIG. 25).

Figure 26C:
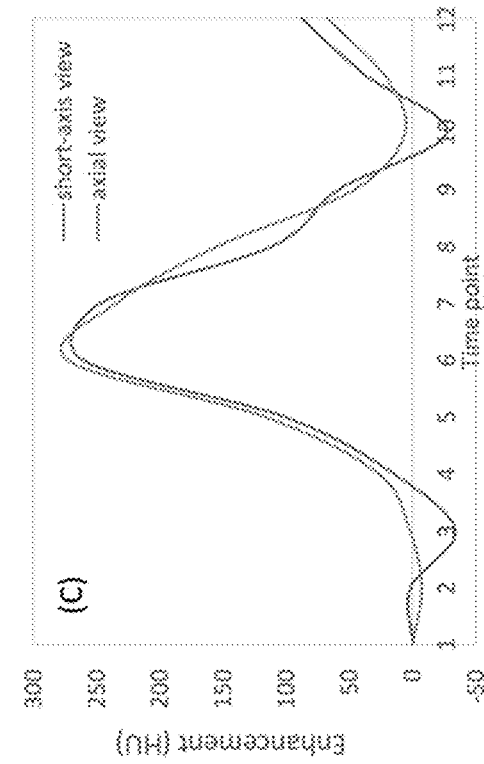
FIG. 26C shows a comparison of the coronary time-enhancement curves sampled at the same spatial location in the left anterior descending artery at the short-axis and axial views.
Figure 26B:
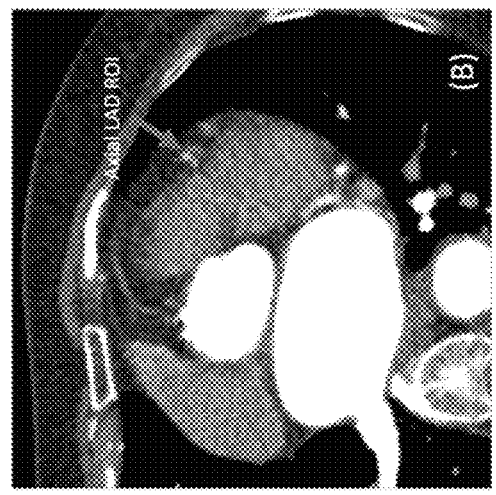
FIG. 26A shows a short-axis view and FIG. 26B shows an axial view of a contrast-enhanced cardiac image of the same patient.
Figure 26A:
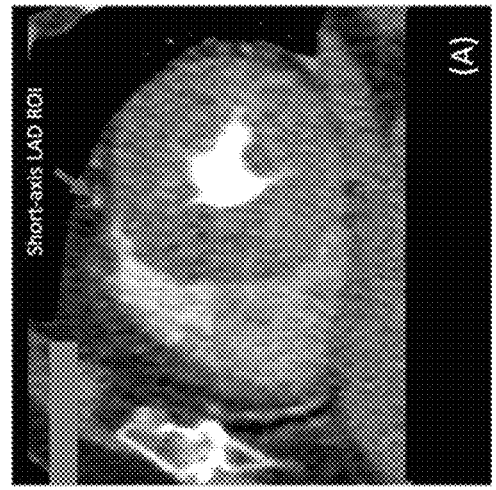
Figure 27A:
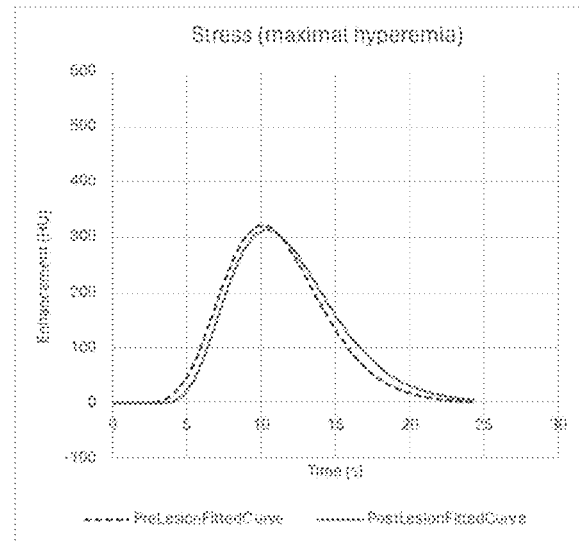
FIG. 27A shows coronary time-enhancement curves sampled at the proximal and distal to a stenosis in the RCA in the stress dynamic perfusion images shown in FIG. 27C.
Figure 27B:
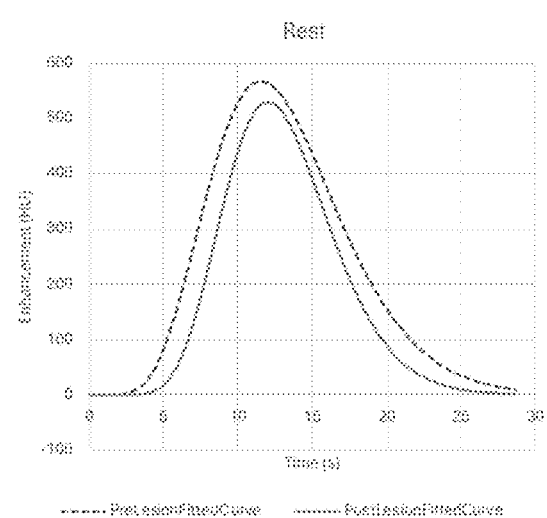
FIG. 27B shows coronary time-enhancement curve sampled at the same locations across the RCA stenosis in the rest dynamic perfusion images shown in FIG. 27D. Note that only the distal sampling location is shown in (FIG. 27C and FIG. 27D.
Figure 27C:
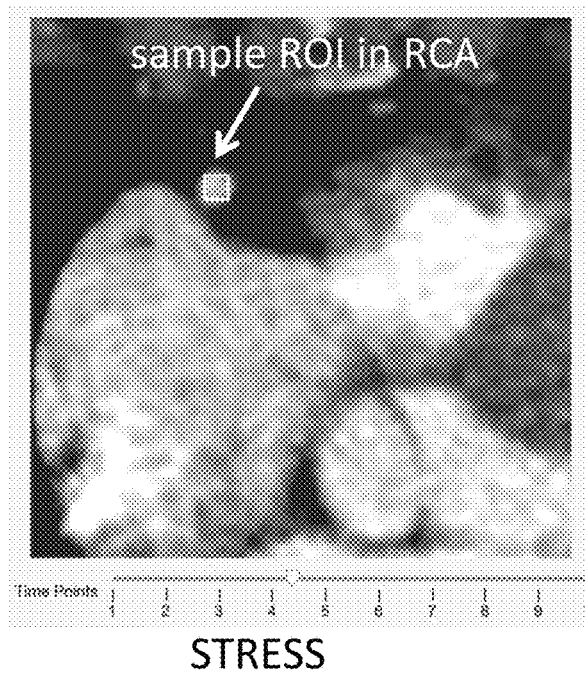
Figure 27D:
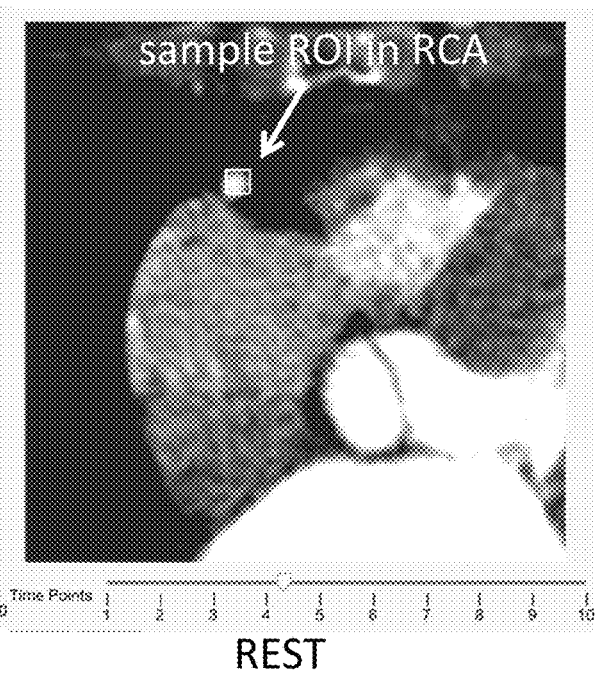

The axial view is the default tomographic plane for CT image reconstruction. As discussed above, for quantitative blood flow assessment, short-axis reformation is necessary to obtain the time-enhancement curves at the slices perpendicular to the direction of blood flow. However, reformatting a full dynamic (4D) image set can be quite time consuming. The proposed ML or DL approach can be used to predict a short-axis time-enhancement curve based on the time-enhancement curve sampled from the axial plane without the need of image reformation. FIG. 26 compares a short-axis time-enhancement curve with an axial time-enhancement curve for one coronary artery. It can be seen that the short-axis curve is slightly more fluctuated than the axial curve. However, the details of the curve shape are irrelevant to the FFR calculation and only the area under the curve matters. This reduces the complexity of the ML and DL learning and makes the proposed methods more feasible for clinical applications.

Experimental Exemplification: Experimental Example 5 (Training a Machine Learning Model to Predict the AUC of a Time-Enhancement Curve During Maximal Hyperemia (Stress) from the AUC of a Time-Enhancement Curve Sampled at Rest)

This example illustrates the machine learning approach to predict the AUC of a time-enhancement curve during maximal hyperemia from the AUC of a time-enhancement curve sampled during the resting condition. While the proposed approach works for both coronary and myocardial time-enhancement curves as well as other cardiovasculatures of interest, an example using coronary time-enhancement curves is provided here. In this approach, the cardiac CT studies with dynamic rest and stress perfusion scans performed on the same patient on the same day were used for training a linear regression model in machine learning. The implementation of machine learning was achieved using Python and Tensor flow. FIG. 27 shows the coronary time-enhancement curves sampled across the RCA (right coronary artery) stenosis in a patient during rest and maximal hyperemia (stress). The sampled coronary time-enhancement curves were denoised with a modified gamma variate function, and the AUC of the denoised (fitted) curve corresponding to the rest condition was used as the input (independent) variable to the machine learning regression. Other input (independent) variables include non-image data such as the patient's age, heart rate and blood pressure measured during the rest condition.

Figure 28:
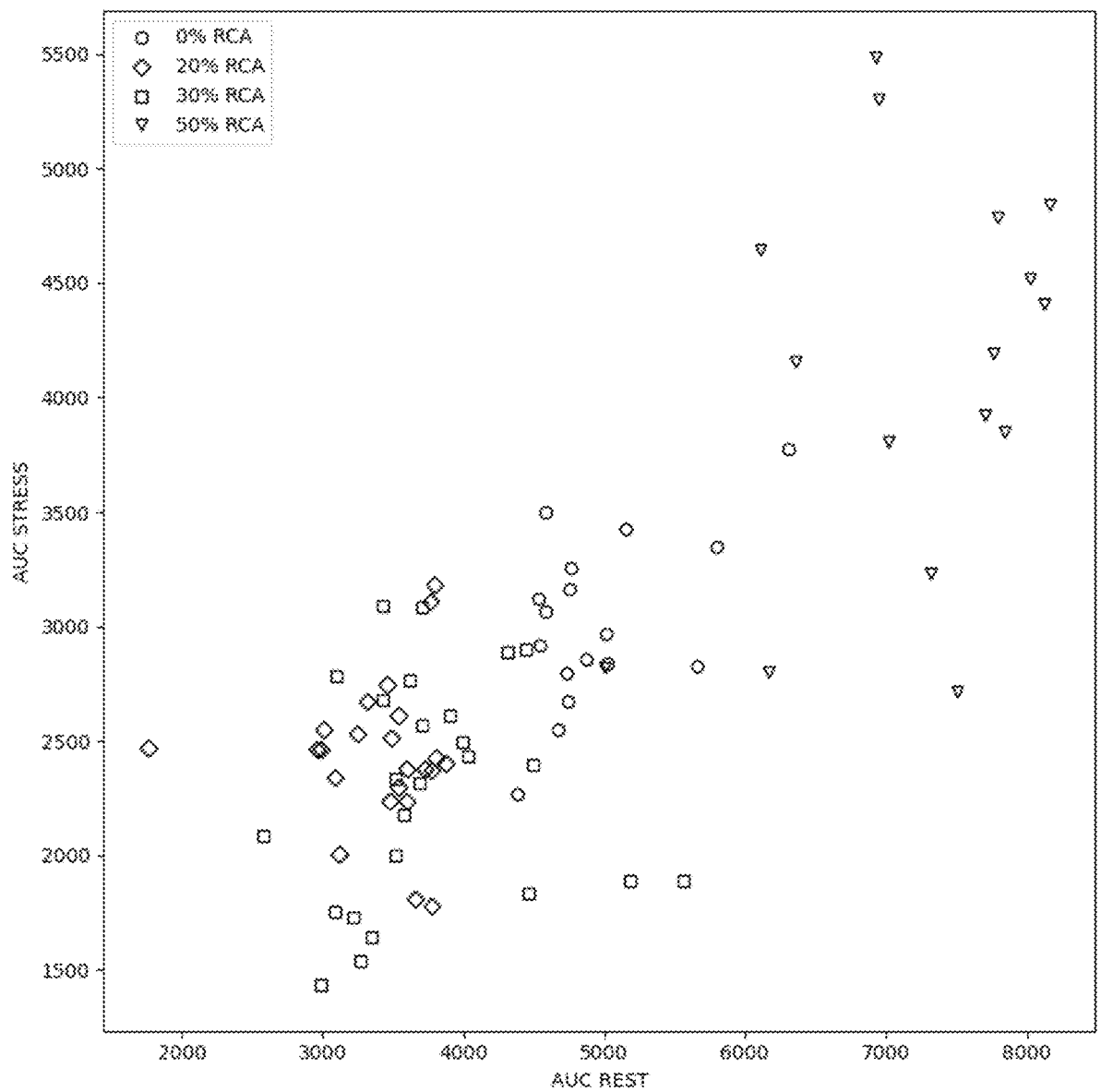
FIG. 28 shows AUCs of stress coronary time-enhancement curves versus AUCs of rest coronary time-enhancement curves sampled in different right coronary arteries with different degree of stenosis (percentage in lumen narrowing). All the data points shown in the graph are true measured AUC values.

FIG. 28 shows the scatter plot of the AUC of the measured stress time-enhancement curve against the AUC of the corresponding measured rest time-enhancement curve sampled in different right coronary arteries with different degrees of stenosis. It can be seen that the AUCs of the rest and stress time-enhancement curves tend to increase with the degree of stenosis in the artery of interest albeit some overlapping between different groups of AUC data.

The AUC data shown in FIG. 28 was divided into the training and test data sets (approximately 80% of the data was used for training) for machine learning. The computer codes shown in FIG. 29 illustrates three hidden layers were implemented in the neural network and linear regression was used for this task.

Figures 30A, 30B:
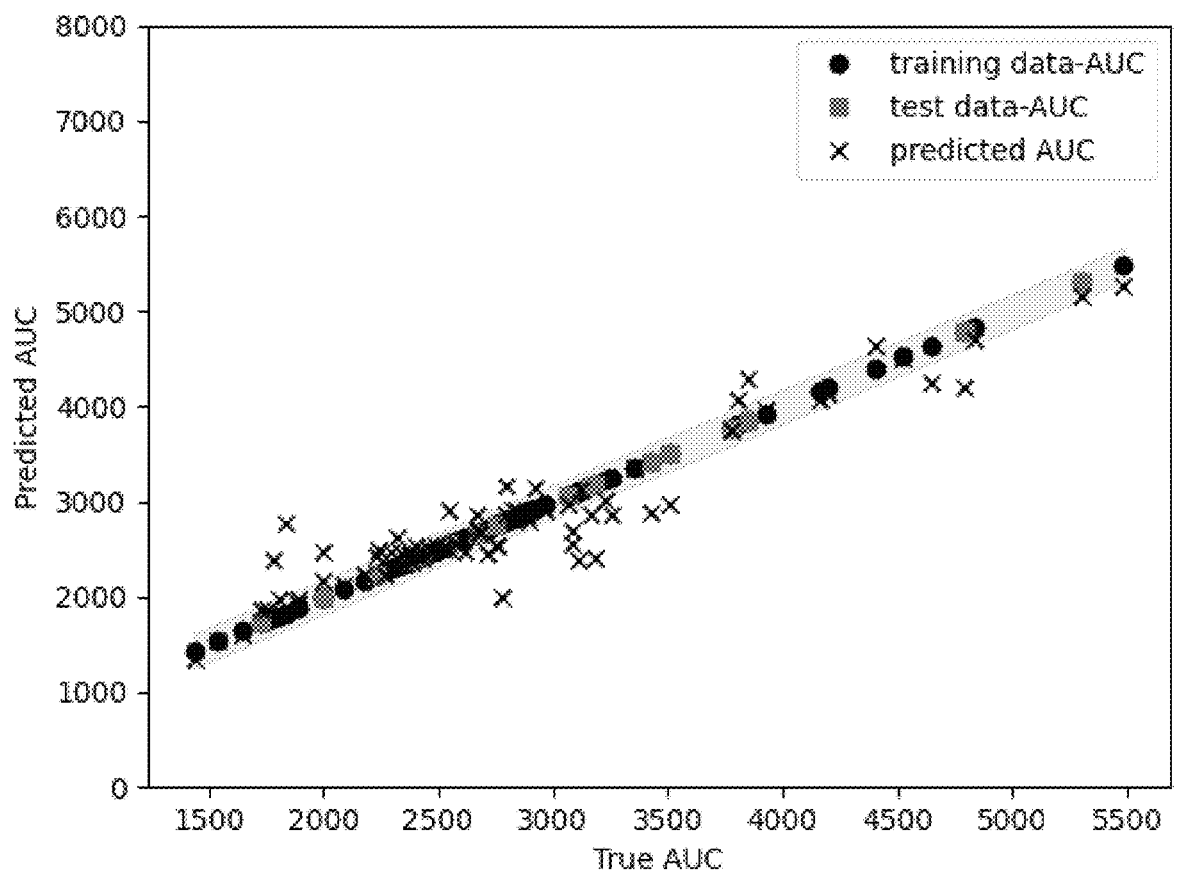
FIG. 30A show predicted stress AUC values (represented by crosses) predicted by the trained machine learning model versus the true stress AUC values measured from stress dynamic perfusion images. The training (circle) and test (square) AUC datasets used for the machine learning model are shown in the background for comparison. The substantial overlap between the crosses and training/test datasets showed the good predictions of stress AUC values made by the model.
FIG. 30B shows the training and test scores and losses associated with the model training.

The training and test results are shown in FIG. 30. The crosses in the graph are the AUCs of the stress coronary time-enhancement curves predicted by the trained neural network against the true AUCs of the stress coronary time-enhancement curves. The training and test scores were 0.904 and 0.837, respectively (the highest score is 1). The results suggest that the trained machine learning model can predict the stress AUC from the measured rest AUC and other non-image data measured at rest (e.g. heart rate, blood pressure) with a high accuracy. The accuracy of the machine learning model can be improved further by training with more image and non-image data and optimizing some of the training settings.

Figure 31:
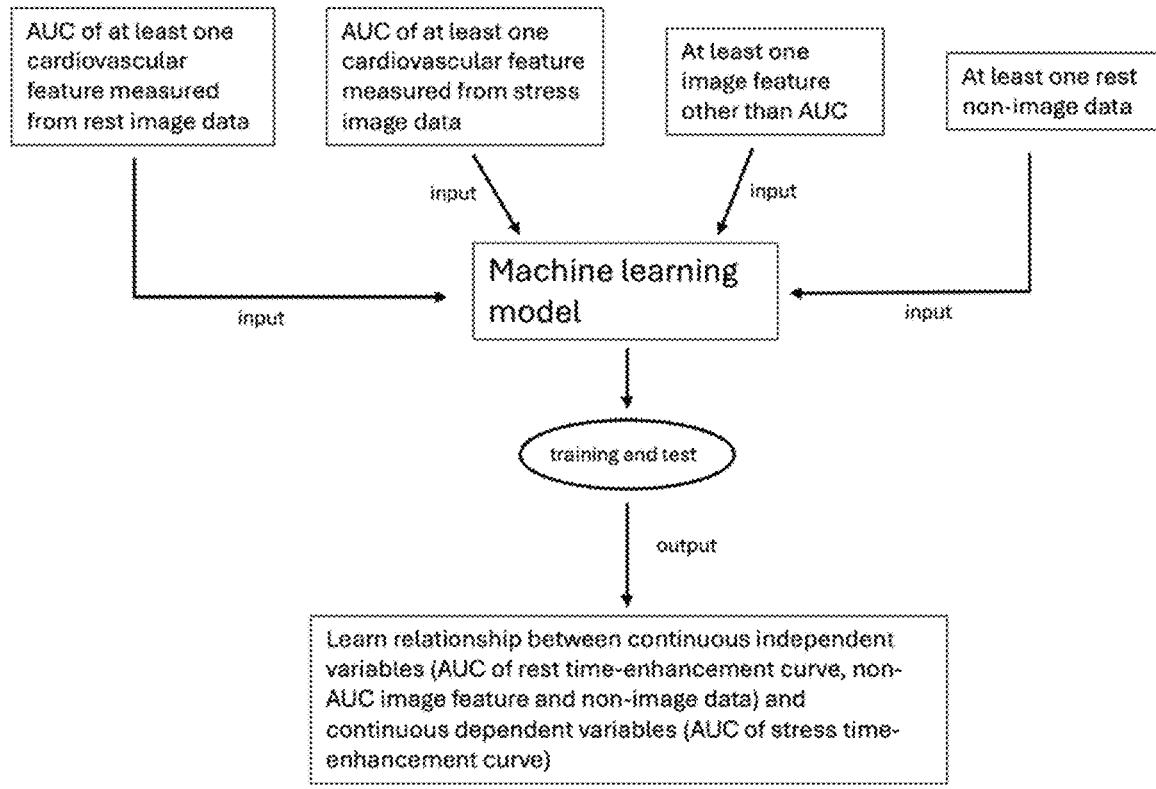
FIG. 31 shows a schematic illustration of the proposed machine learning approach to predict the area under curve (AUC) of a time-enhancement curve at stress (maximal hyperemia) without actually acquiring the curve. The input AUC can be a coronary or myocardial time-enhancement curve. Likewise, the output AUC can be a coronary or myocardial time-enhancement curve. Because these curves are closely related to each other. Coronary AUC can be used as the input to predict myocardial AUC, or vice versa. These curves can also be used concomitantly as the input training data for the machine learning model.
Figure 32:
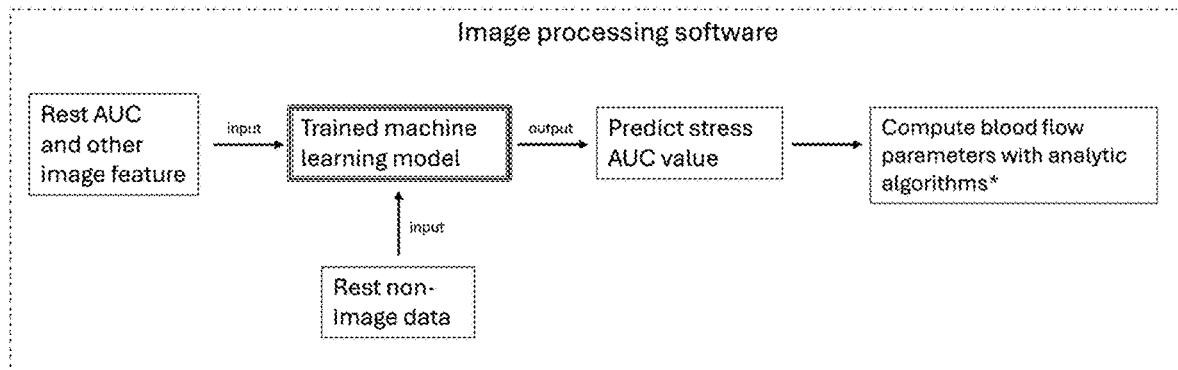
FIG. 32 shows a schematic illustration of how the trained machine learning model can be integrated into an existing image processing software to facilitate prediction of blood flow parameters corresponding to maximal hyperemia. The asterisk (*) is to note that the algorithms were described in co-owned PCT/CA2019/050668 filed 16 May 2019 or in co-owned PCT/CA2021/051189 filed 26 Aug. 2021.

The flow diagram in FIG. 31 illustrates the machine learning scheme performed in this example. The flow diagram in FIG. 32 illustrates how the trained machine learning model can be used for clinical hemodynamic assessment.

Experimental Exemplification: Experimental Example 6 (Training a Machine Learning Model to Predict the AUC of a Full Time-Enhancement Curve from the AUC of a Truncated Time-Enhancement Curve)

Figure 33A:
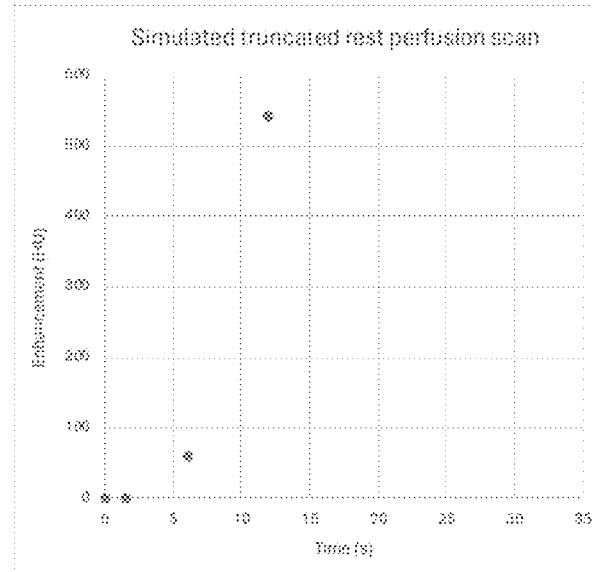
FIG. 33A shows a truncated perfusion dataset generated by removing data points after peak enhancement.
Figure 33B:
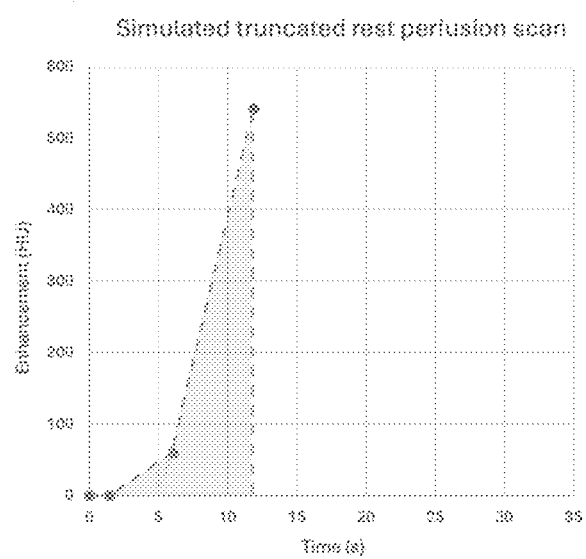
FIG. 33B shows AUC (shaded area) computed for the generated truncated data set, which was used for machine learning.

This example illustrates a machine learning approach to predict the AUC of a full coronary time-enhancement curve from a truncated coronary time-enhancement curve sampled from a simulated truncated rest perfusion scan. As mentioned before, a full curve is defined as the one covering the baseline and the entire upslope and downslope. Prior to the training, a pseudo truncated perfusion scan was first simulated by removing the images after the peak enhancement in the dynamic perfusion images (FIG. 33a). The AUC of the truncated curve was then computed (FIG. 33b). This AUC with that of the full (untruncated) curve were used as a pair of input variables to train a machine learning linear regression model to understand the relationship between the two AUC values and make correction prediction for unseen cases.

The curve shown in FIG. 33 is a simulation of a pseudo truncated time-enhancement curve synthesized by combining the image data from a bolus tracking (BT) scan with the image data from the subsequent diagnostic CT angiography (CTA) scan. The simulation is based on a realistic clinical scenario where the diagnostic CTA scan is triggered approximately 4 to 7 seconds after the trigger threshold in the monitor region is reached (the trigger threshold in the selected monitor region is set to 50 HU in this simulation and the trigger time gap is specific to each scanner and is a function of time to reconfigure the scanner for BT scan settings to diagnostic CTA scan settings). Therefore, the truncated time-enhancement curve has a larger time gap between the 3rd and the 4th data points. Besides perfusion scan, the proposed machine learning approach will work for any type of scan, including test bolus (TB) scan, bolus tracking (BT) scan, and diagnostic CTA scan. Although the contrast volume and X-ray energy used for each scan may be different (Table 1), the computation of AUC should not be affected if the conversion from image pixel enhancement to tracer (iodine) concentration can be performed using a conversion factor specific to the X-ray energy used for the scan.

TABLE 1

Comparison in contrast volume and X-ray energy used between different CT scans (for cardiac).

| | Contrast volume injected | X-ray energy setting |
|---|---|---|
| Dynamic Perfusion Scan | ~50 mL | 80, 100 or 120 kV |
| Test Bolus Scan | 15-20 mL | 80 or 100 kV |
| Bolus Tracking Scan | 60-80 mL | 80 or 100 kV |
| Diagnostic CTA Scan | | |

Figure 34:
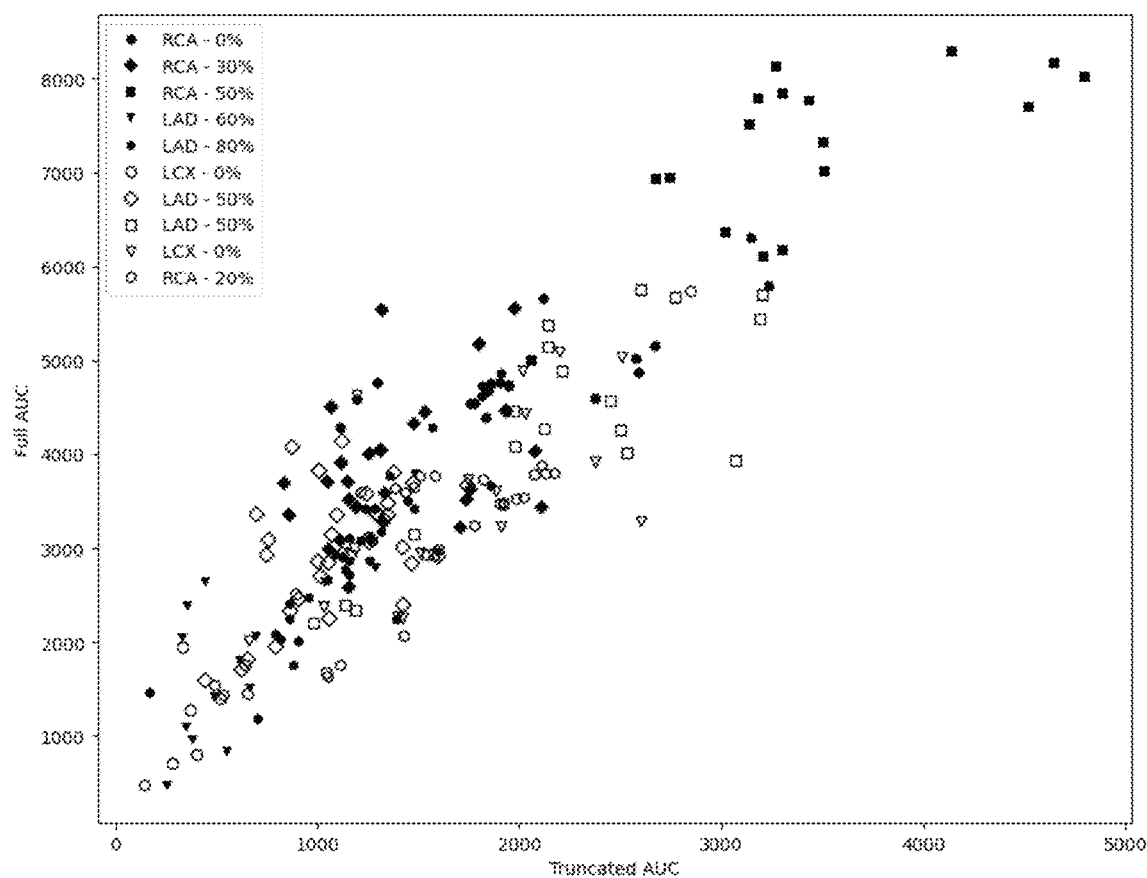
FIG. 34 shows AUCs of full time-enhancement curves sampled from dynamic perfusion images versus AUCs of truncated time-enhancement curves generated from the full curves for different coronary arteries with different degrees of stenosis.

FIG. 34 shows the scatter plot of the AUC of measured full time-enhancement curve against the AUC of related measured truncated time-enhancement curve sampled from different coronary arteries with different degrees of stenosis. The AUC data was divided into the training and test datasets for machine learning (approximately 80% was used for training). Similar to Experimental Example 5, a linear regression analysis was used in machine learning for this task. The preliminary training results (FIG. 35) showed a high train/test score and a low train/test score, suggesting the trained machine learning regression model can be used to predict the AUC of a full coronary time-enhancement curve even if the time-enhancement curve is not acquired completely to cover the entire upslope and downslope.

Figure 36:
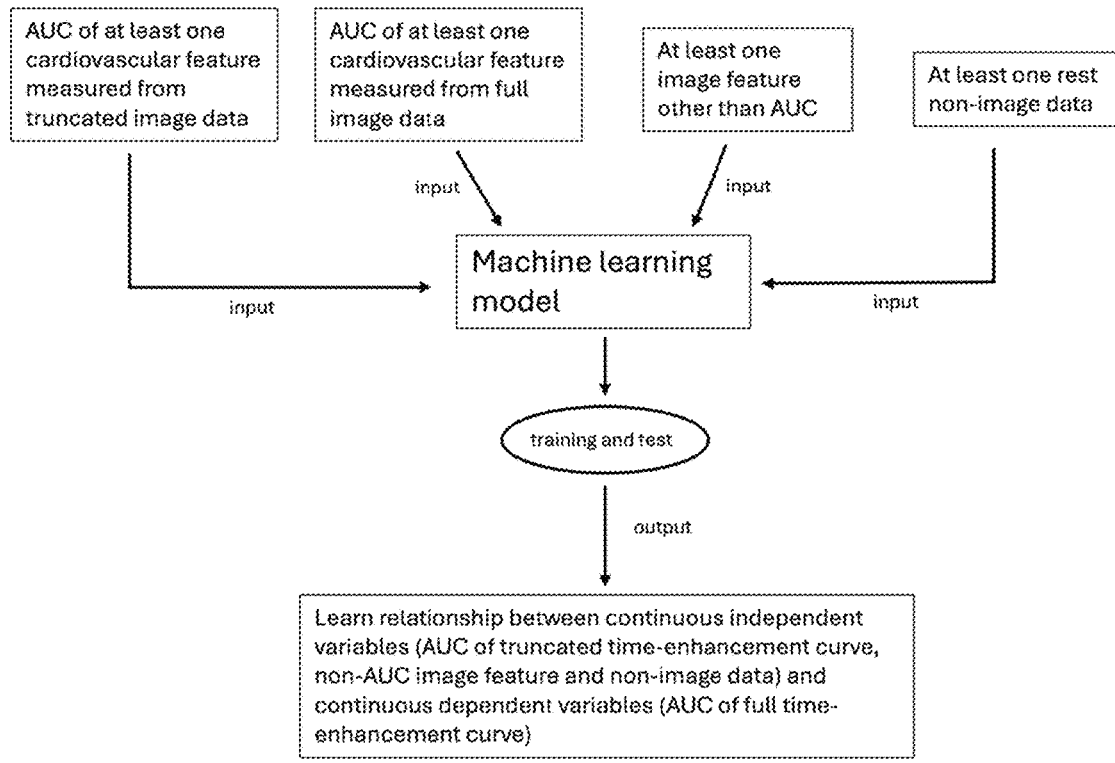
FIG. 36 illustrates a machine learning scheme discussed in Example 6.
Figure 37:
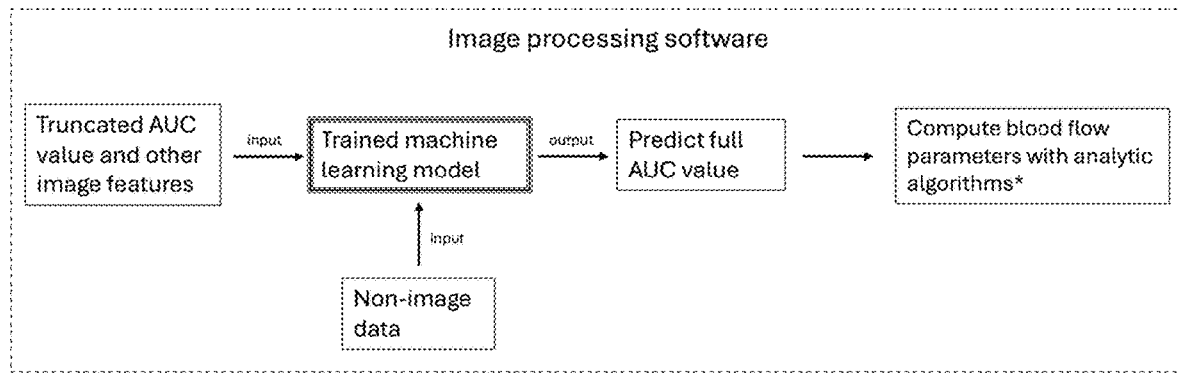
FIG. 37 illustrates how the trained machine learning as trained according to the scheme shown in FIG. 36, can be used for clinical hemodynamic assessment. The asterisk (*) is to note that the algorithms were described in co-owned PCT/CA2019/050668 filed 16 May 2019 or in co-owned PCT/CA2021/051189 filed 26 Aug. 2021.

The flow diagram in FIG. 36 illustrates the machine learning scheme discussed in this example. The flow diagram in FIG. 37 illustrates how the trained machine learning can be used for clinical hemodynamic assessment.

Experimental Exemplification: Experimental Example 7 (Training a Machine Learning Model to Predict the AUC of a Time-Enhancement Curve in the Short-Axis Tomographic View from the AUC of a Time-Enhancement Curve in the Default Axial Tomographic View)

As illustrated in FIG. 26, coronary time-enhancement curves can be sampled from dynamic cardiac perfusion images at different tomographic orientations. In CT, the default image view is axial, but a perfect cross-sectional view of the arterial lumen may not be seen in a given axial slice (ie., an axial slice may have a non-orthogonal orientation relative to a central longitudinal axis of a blood vessel or relative to direction of blood flow). Currently, reformatting the axial images into the short-axis orientation (ie., a slice having an orthogonal orientation relative to a central longitudinal axis of a blood vessel or direction of blood flow) requires a specialized software to perform volumetric image reformation. FIG. 38 shows the preliminary results of using a similar machine learning approach to those described in Experimental Examples 5 and 6 to predict the AUC of a coronary time-enhancement curve in a short-axis tomographic slice from the AUC of a coronary time-enhancement curve sampled in the corresponding axial slice.

Experimental Exemplification: Experimental Example 8 (Training a Deep Neural Network for Segmenting the Coronary Arteries and Myocardium in Contrast-Enhanced Cardiac CT Images)

In contrast to the approaches discussed in Experimental Examples 5 and 6, this example illustrates a deep learning approach for segmenting the coronary arteries and myocardium in contrast-enhanced cardiac CT images. Such segmentation facilitates relevant image features to be extracted to generate input variables for the subsequent machine learning. In other words, this approach is a combination of deep learning and machine learning. FIGS. 39A and 39B show the labeling of different image features, including the coronary arteries, ascending aorta and left ventricular myocardium, with different colours using the MATLAB's Medical Image Labeler. These image labels were used to train a deep neural network called U-NET for segmenting these features in unseen contrast-enhanced cardiac CT images. The computer codes shown in FIG. 39C demonstrate the implementation of a three-dimensional U-NET using MATLAB. The U-NET is based on a convolution neural network (CNN) mentioned in previous sections but with some modifications that can yield a more precise segmentation than CNN. The main difference between the two neural networks is that in CNN, an image is downsampled and converted into a vector which is used for object classification. On the contrary, in U-NET, an image is downsampled to a pixel level followed by upsampling. The additional sampling step allows U-NET to achieve a more precise detection of the structure details in the image. In other words, the CNN approach can provide information about what an object in the image is, whereas the U-NET approach can also provide this information plus the detailed spatial information about the object (where exactly the object is located in the image).

The segmentation task requires an excellent spatial resolution to accomplish, because the cardiovasculature of interest (such as a coronary artery) may not stay in the exact same location during a time-series of scan images (such as obtained in a dynamic perfusion scan) due to the patient's residual respiratory and cardiac motion during image acquisition. Therefore, a deep neural network that can better preserve the spatial information of the images (i.e. U-NET) is more suitable than a deep neural network that is less capable of preserving the spatial information of the images (i.e. CNN) for our task. Examples of medical image segmentation with U-NET and CNN have been previously described (Ronneberger, O., Fischer, P., Brox, T. (2015). U-Net: Convolutional Networks for Biomedical Image Segmentation. In: Navab, N., Hornegger, J., Wells, W., Frangi, A. (eds) Medical Image Computing and Computer-Assisted Intervention—MICCAI 2015. MICCAI 2015. Lecture Notes in Computer Science, vol 9351. Springer, Cham) (Krizhevsky A, Sutskever I, Hinton GE (2012) ImageNet classification with deep convolutional neural networks. Adv Neural Inf Process Syst 25).

Due to the large number of CT images in a dynamic perfusion scan covering the whole heart (e.g. 14 cm axial scan coverage with 1 mm image slice thickness) and large number of pixels in each CT image (512×512), Image segmentation with U-NET requires a powerful computer to achieve. For example, the minimum requirement for RAM is typically 64 GB and the graphic card can be a NVIDIA RTX 3060 Ti (8 GB GDDR6). However, the preferred hardware requirement is usually higher to ensure an efficient deep learning. For example, a NVIDIA RTX A5000 graphic card (24 GB GDDR6) has been used by some researchers for deep learning. Therefore, a standard laptop or desktop computer built for non-heavy duties is likely not suitable for this task.

Figure 40:
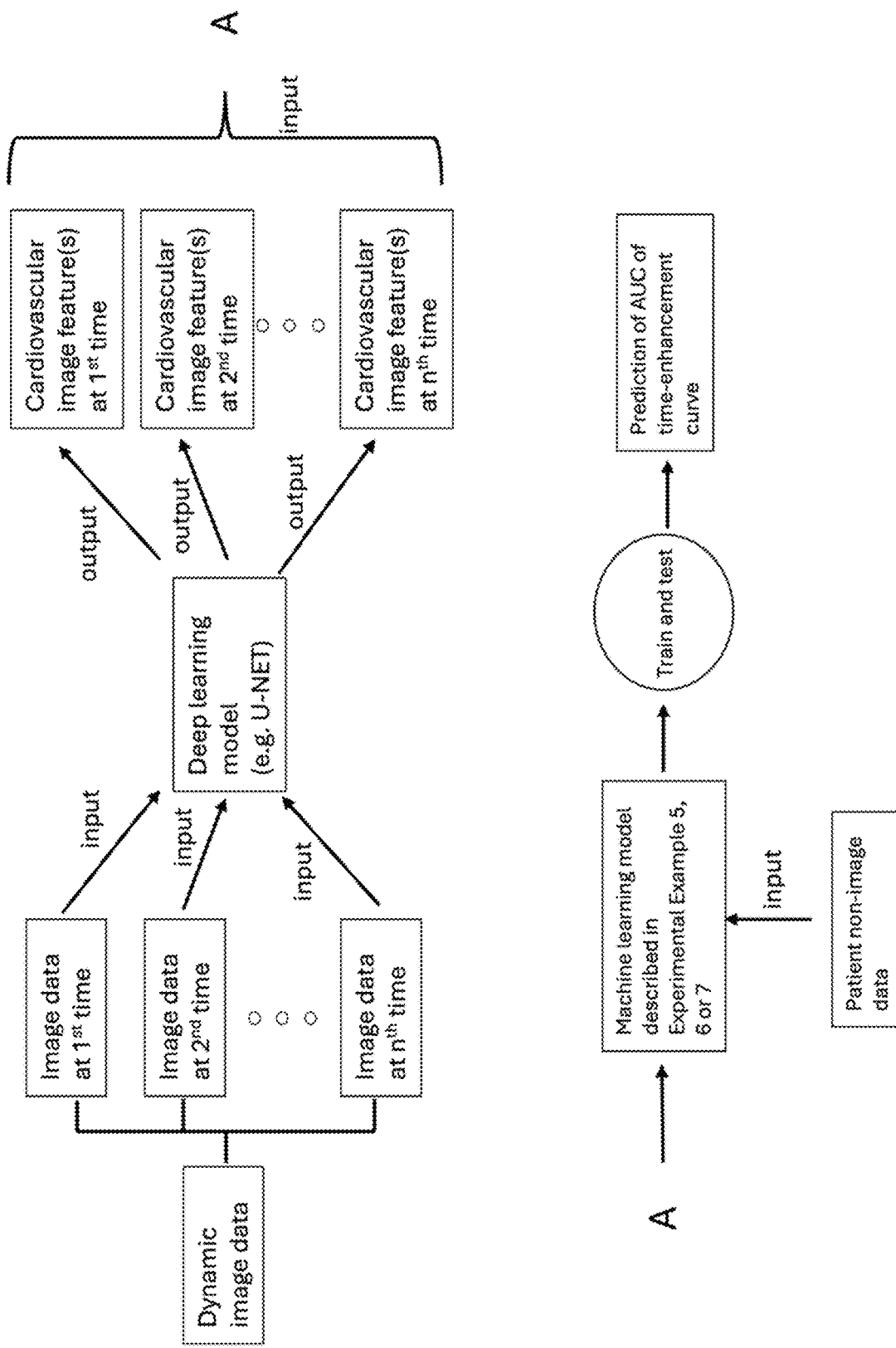
FIG. 40 illustrates how the training results from a deep learning model can be used as the input labels to train a machine learning model described in Examples 5-7.

Approximately 60 and 20 contrast-enhanced cardiac CT image sets were used for training and testing the U-NET, respectively. Each CT image sets had labels for coronary artery (i.e. RCA, LAD, LCX and LM) and the background (any feature unrelated to the coronary arteries). We first focused on training the U-NET for segmenting the left main (LM) and the left circumflex (LCX), and the test accuracy for segmenting the LM and LCx was 70.5%. A higher test accuracy can be expected by using more complex image sets for training and adjusting the training settings such as the learning rate. FIG. 40 illustrates how the training results from a deep learning model can be used as the input labels to train a machine learning model described in Experimental Examples 5-7.

As demonstrated above, a use of machine learning model can significantly streamline the clinical workflow associated with blood flow imaging by employing a hybrid computer-learning-analytic approach. As explained in co-owned PCT/CA2019/050668 filed 16 May 2019 or in co-owned PCT/CA2021/051189 filed 26 Aug. 2021, blood flow variables are dependent on many other physiological and morphological variables. If a computer needs to learn the relationship between each individual blood flow variable and all of its dependent variables, it will require a very large amount of training/validation data, image feature extractions and labeling, and computation time. The approach described herein restricts the computer learning to a relevant and central parameter, such as the area under a time-enhancement curve (AUC), which is needed for the analytic steps to derive all the blood flow characteristics described in co-owned PCT/CA2019/050668 filed 16 May 2019 or in co-owned PCT/CA2021/051189 filed 26 Aug. 2021.

Advantageous features of the currently disclosed hybrid computer-learning-analytic blood flow imaging approach are numerous, including for example predicting a hyperemic time-enhancement curve from a rest time-enhancement curve, predicting a hyperemic time-enhancement curve at a microvascular level from a macrovascular rest time enhancement curve, or predicting a time-enhancement curve at one location in a blood vessel in one orientation from a time-enhancement curve sampled at the same location in a blood vessel in another orientation.

The currently disclosed hybrid computer-learning-analytic blood flow imaging approach can offer reliable functional assessment of vascular diseases with CT while simplifying the clinical workflow through:
1. deriving blood flow characteristics without performing a genuine dynamic perfusion scan or performing a short or truncated dynamic perfusion scan.
2. deriving blood flow characteristics without administering a vasodilator.
3. deriving blood flow characteristics without reformatting a dynamic (four-dimensional) image set from one tomographic view to another.

Several illustrative variants of a method or system for blood flow imaging have been described above. Further variants and modifications are described below. Moreover, guiding relationships for configuring variants and modifications are also described below. Still further variants and modifications are contemplated and will be recognized by the person of skill in the art. It is to be understood that guiding relationships and illustrative variants or modifications are provided for the purpose of enhancing the understanding of the person of skill in the art and are not intended as limiting statements.

For example, the blood flow imaging method 20 as shown FIG. 2 is merely illustrative, and should not be considered as limiting to the blood flow imaging method as one or more steps shown in FIG. 2 can be substituted or removed as desired for a specific implementation. For example, in a specific implementation CT scanning of a subject may be geographically or temporally displaced from image reconstruction. An example, of a contemplated variant blood flow imaging method includes both projection data from CT scanning and image reconstruction occurring at a prior stage and reconstructed images are stored for analysis at either a later date or for analysis by a third party. The variant blood flow imaging method can initiate by obtaining the stored image data. Contrast agent signal data can then be extracted from the stored image data, optionally without explicitly identifying a target blood vessel in the image data. A time-enhancement curve is generated based on the contrast agent signal data, the time-enhancement curve having an upslope plotted from data points obtained during an increase phase of the contrast agent signal data, and a downslope plotted from data points obtained during a decline phase of the contrast agent signal data. A flow velocity value is then determined according to the same method steps shown in FIG. 6A or FIG. 6B.

As another example, the blood flow imaging method and system are not limited to computed tomography (CT) scanning, and can readily be adapted to other imaging modalities that have sufficient spatial resolution to image blood vessels and exhibit proportional increase in signal intensity in a ROI as a function of the mass of contrast agent present in the ROI (more contrast agent or tracers results in a higher signal in the ROI), including MRI and other X-ray imaging techniques (ie., X-ray imaging techniques other than CT imaging), including for example fluoroscopy. X-ray based scans are a form of medical imaging comprising transmission of a high frequency electromagnetic signal that becomes attenuated as it passes through the body of a subject with the remaining signal captured by a detector for subsequent analysis. Data for the Experimental Examples was acquired with a single-energy CT (SECT) scanner. Most clinical CT scanners use single-energy acquisition. However, dual-energy CT (DECT) scanners are also available. Dual-energy CT refers to two X-ray energy sources used for scanning an object instead of a single X-ray energy source. Existing literature shows that dual-energy CT can perform dynamic CT acquisition just like single-energy CT. From the image processing aspect, nothing changes and methods described herein or in co-owned PCT/CA2019/050668 filed 16 May 2019 or in co-owned PCT/CA2021/051189 filed 26 Aug. 2021, such as methods based on Reynolds Transport Theorem or Indicator-Dilution Principle or Bernoulli's equation, can be applied in both SECT and DECT.

An alternative to X-ray based scans is Magnetic Resonance Imaging (MRI), which has well-recognized medical imaging applications including for example, imaging to diagnose disease in soft tissues such as the brain, lungs, liver, muscles, and heart. MRI scans involve the application of a magnetic field to a patient and the transmission of radio frequency pulses. Resonance energy is emitted by the patient and picked up by a receiver/detector that captures scan data for subsequent analysis. To improve image clarity, both X-ray scans and MRI scans involve the oral or intravenous administration of a contrast agent to a patient. Contrast agents for X-ray imaging techniques include for example iodine-based contrast agents. Contrast agents for MRI imaging techniques include for example gadolinium-based contrast agents. Scan data acquired from X-ray based scanner devices/systems are often referenced as scan data or projection data interchangeably, while scan data acquired from MRI scanner devices/systems are typically referenced as scan data. Thus, the term scan data is understood to encompass the term projection data.

The methods described herein and as adapted from co-owned PCT/CA2019/050668 filed 16 May 2019 or in co-owned PCT/CA2021/051189 filed 26 Aug. 2021, demonstrated with dynamic contrast-enhanced CT imaging data obtained after an intravenous bolus injection of iodine-based contrast agent, are also applicable for dynamic MRI imaging data obtained after intravenous bolus injection of Gadolinium-based (Gd) contrast agent. We have demonstrated with a preclinical study in co-owned PCT application no. PCT/CA2019/050668 (filed 16 May 2019) that a time-enhancement curve in a region of interest can be obtained from dynamic contrast-enhanced MRI imaging in a similar manner to dynamic contrast-enhanced CT imaging. Furthermore, the temporal change in signal intensity (e.g. Ti relaxation time) over time is induced by the movement of Gd contrast agent in the region of interest, and the magnitude of signal alteration is closely related to the concentration of Gd-based molecules (tracers). When a low concentration of Gd contrast agent is used, the change in MRI signal intensity and contrast concentration in a region of interest exhibits a relatively linear relationship. Moreover, with respect to co-owned PCT/CA2021/051189 filed 26 Aug. 2021, this linear relationship facilitates the estimation of the time rate of change of mass of tracer (dm/dt in Equation 11 in co-owned PCT/CA2021/051189 filed 26 Aug. 2021) with the RTT method to derive flow velocity.

Contrast agents (also referred to as tracers) for various imaging modalities are established in the current literature and continue to be an active area of development for new alternatives. The blood flow imaging method and system may accommodate any suitable combination of contrast agent and imaging modality provided that the imaging modality affords sufficient temporal and spatial resolution to image a cardiovasculature of interest, for example a blood vessel of interest or a portion of a blood vessel of interest or a heart chamber of interest or a portion of a lumen of a heart chamber of interest.

The blood flow imaging method and system can include a selection of a target voxel or pixel in the acquired image data (ie., acquired pixel data) or image data outputted by a computer learning model and analysis of the pixel data in the selected voxel or pixel. While voxels provide precision to volumetric imaging, voxel based assessment can also be disadvantaged by large data sets that are unwieldy to manage given the bandwidth of common computers. The systems and methods described herein provide an efficient manipulation of large data files that permits interactive visualization and fine temporal resolution with near real-time assessment using commonly available computers.

A voxel is the smallest 3D element of volume and is typically represented as a cube or a box, with height, width and depth dimensions (or 3D Cartesian coordinate x, y and z dimensions). Just as 2D images are made of several pixels (represented as squares, with height and width, or x and y dimensions) and the smaller the pixel the better the quality of the picture, the same concept applies to a 3D data volume. In data acquisition, each three-dimensional voxel represents a specific x-ray absorption. A voxel stated as isotropic means that all dimensions of the isotropic voxel are the same and typically the isotropic voxel is a perfect cube, with uniform resolution in all directions. In contrast, a voxel stated as anisotropic or non-isotropic means that the anisotropic voxel is not a perfect cube, such that all dimensions of the voxel are not the same (ie., at least one dimension of the anisotropic voxel is different than other dimensions) or that the anisotropic voxel includes partial voxel units (typically more than one voxel unit). The systems and methods described herein provide an efficient manipulation of image data that permits operability with selection of one or both of isotropic or non-isotropic target voxels.

The terms ROI and target voxel are related, as an ROI in reconstructed 3D image data will encompass either a target voxel or a block of neighboring target voxels. In reconstructed 2D image data, an ROI will encompass either a target pixel or a block of neighboring target pixels, and therefore the terms ROI and target pixel are also related. The terms voxel and pixel are related as voxel is a 3D analog of a pixel. Voxel size is related to both the pixel size and slice thickness. Pixel size is dependent on both the field of view and the image matrix.

A selected isotropic target voxel may be a single isotropic voxel or a continuous block of neighboring or adjacent voxels where the block is isotropic. A selected non-isotropic target voxel will typically encompass more than one voxel unit, but may approach a volume of a single voxel unit or may be a continuous block of neighboring or adjacent voxels where the block is non-isotropic. A non-isotropic block of voxels can include parts of voxels at its boundary as would be expected if the target voxel is a non-square shape such as a circle or triangle. Thus, blocks of target voxels or target pixels need not be limited to full voxel or pixel units as an ROI of various shapes (including circles, triangles or even irregular shapes) may be accommodated, and an ROI may defining a block of neighboring voxels or pixels with partial voxels at the boundary of the ROI.

The elapsed time of an imaging scan procedure, equivalent to the time duration of scan data acquisition, can be varied as desired provided that the imaging scan captures at least a portion of an increase phase or a decline phase of contrast agent at the sampling site so as to obtain sufficient data to estimate or predict area under the time-enhancement curve. Generally, to capture a portion of both increase and decline phases an imaging scan of greater than 5 seconds is needed. In certain examples, imaging scans can be configured to capture scan data for greater than 6 seconds, greater than 7 seconds, greater than 8 seconds, greater than 9 seconds or greater than 10 seconds. Although not constrained by an upper time limit and not constrained by the transit time of contrast agent, most often imaging scans will not extend significantly beyond the expected transit time of contrast agent at a sampling site.

The number of images (also referred to as frames or individual scans) analyzed to predict the area under the time-enhancement curve can be varied as desired provided that the number of images cumulatively captures at least a portion of an increase phase or a decline phase of contrast agent at the sampling site so as to obtain sufficient data to estimate shape of the time-enhancement curve. Generally, to capture both increase and decline phases an imaging scans of greater than 5 images is needed. In certain examples, imaging scans can be configured to capture scan data for greater than 6 images, greater than 8 images, greater than 10 images, greater than 12 images, greater than 14 images, greater than 16 images, greater than 18 images, or greater than 20 images. Additionally, imaging scans configured to capture at least 10 images are observed to benefit consistency of peak value determinations and curve shape; signal intensity values need not be extracted from all of the at least 10 images, but the at least 10 images often provides a large enough set of images to select a subset of appropriate time-distributed images (typically 5 or more images) that leads to consistency of estimating curve shape.

The blood flow imaging method and system is considered dynamic due to analysis of a plurality of images as distinguished from static techniques that evaluate a single image. Most commercially available CT angiography techniques are static. Furthermore, commercially available CT angiography techniques that are minimally dynamic (evaluating 2 to 3 images) do not recognize or consider benefits of acquiring scan data from both the increase phase and decline phase of contrast agent transit or generating a time-enhancement curve or predicting an area under a time-enhancement curve using a computer learning model. Furthermore, CT angiography studies that obtain 2 or 3 images at slightly different time frames, for motion correction, or for the doctor to select the best image that is least affected by motion, may also be considered a static technique.

A plurality of images, for example at least 5 images, for predicting an area under a time-enhancement curve are considered to be a plurality of corresponding images with the correspondence of images referring to a time-ordered sequence of multiple images located in the same sampling site or slice or in a group of adjacent sampling sites or slices. Thus, correspondence of images is spatially limited to a single sampling site or slice or a group of adjacent sampling sites or slices (or to a single ROI or a group of adjacent ROIs), and correspondence of images does not include sampling sites or slices spatially separated to be upstream versus downstream of a source of blood flow aberration. For example, when determining a blood flow characteristic comprises a comparison of corresponding values calculated from first and second time-enhancement curves, the first time-enhancement curve may be from a first plurality (or set) of corresponding images from a first sampling site or slice located upstream of a suspected source of a blood flow aberration and the second time-enhancement curve may be from a second plurality (or set) of corresponding images from a second sampling site or slice located downstream of the suspected source of the blood flow aberration. In this example, the first set of corresponding images will not be intermingled with the second set of corresponding images as the first and second sampling sites are spatially separated by an intervening suspected source of blood flow aberration.

Each set or plurality of corresponding images is optionally time-ordered or time-resolved to benefit input to a computer learning model to predict an area under a time-enhancement curve. The time-enhancement curve can have an upslope, a peak and a downslope. Time-ordering benefits computer learning and computer prediction of an area under the time-enhancement curve. Time-ordering provides an upslope of the time enhancement curve interpolated from time-specific contrast agent signal data points acquired during an increase phase of contrast agent transit, and the downslope of the time enhancement curve interpolated from time-specific contrast agent signal data points acquired during a decline phase of contrast agent transit. Accordingly, acquisition of scan data and reconstruction of image data occurs with reference to a time-ordering scheme such that each set of corresponding images obtained from the image data can be arranged in a time-ordered sequence. A time-ordering scheme can be any convenient scheme including a time stamp with a real-time identifier, a relative-time identifier such as elapsed time from bolus injection, or any customized time identifier that can be used for identifying absolute or relative time of each image and time-resolved sequencing of the set of corresponding images. Established protocols for time intervals between contrast agent administration and image acquisition may be adopted in devising a time ordering scheme. Furthermore, established timing techniques, for example bolus tracking, may be adopted to optimize timing of scan acquisition and time-ordering of image data.

The time-enhancement curve is a plot of contrast agent signal intensity versus time derived from scan data of a contrast agent transit at a single sampling site or a group of adjacent sampling sites. The time-enhancement curve may also be referred to as a time-density curve, signal intensity time curve, time-dependent signal intensity, time-intensity curve among other variations. The machine learning model does not need to plot a time-enhancement curve (plots shown in the Figures are for illustration for easier comparison to technology described in co-owned PCT/CA2019/050668 filed 16 May 2019 or in co-owned PCT/CA2021/051189 filed 26 Aug. 2021) and can predict an area under a time-enhancement curve directly from inputted images by directly assessing enhancement with the inputted images or selected portions therein. The term enhancement within the term time-enhancement curve refers to an increase in measured contrast signal intensity relative to a baseline or reference value such as signal intensity measured at a minimal level of contrast agent or measured at a residual level of contrast agent or measured in absence of contrast agent. Qualitative terms describing a contrast agent transit, such as prior to entry, entry, wash-in, increase phase, decline phase, wash-out, clearance and subsequent to clearance, are referenced to a bolus injection event or more generally a contrast agent administration event, such that each of these terms, except prior to entry, describing a portion of a contrast agent transit that occurs subsequent to an associated injection or administration event. The term prior to entry may correspond to a time range that may begin earlier than the injection or administration event.

The blood flow imaging method and system described herein allows for determination of a blood flow characteristic. A blood flow characteristic may be any metric that assesses blood flow at a region of interest in a subject. A blood flow characteristic includes those described in co-owned PCT/CA2019/050668 filed 16 May 2019 or in co-owned PCT/CA2021/051189 filed 26 Aug. 2021, for example, flow rate, flow velocity, flow acceleration, flow pressure and reconstruction of heart-induced pulsation. Heart-induced pulsation refers to temporal variation of flow rate/flow velocity arising from the heart contraction and relaxation (which lead to forward ejection and backward suction of blood respectively). Rate, velocity, and acceleration are metrics of blood flow. The blood flow imaging technique can include other blood flow assessment techniques as desired, for example blood flow assessment or blood pressure assessment (using Bernoulli's equation) as described in co-owned International PCT Application No. PCT/CA2019/050668 filed 16 May 2019 which also describes fractional flow reserve (FFR) and shear stress as blood flow characteristics that may be quantified; and also describes area under the curve, rate of change of area under the curve, peak (maximum value) of the curve, and blood volume as further examples of a blood flow characteristic.

A blood flow characteristic can be determined from raw signal intensity measurement or enhancement measurements. In CT, measured signal intensity can be stated as CT number, while enhancement infers a normalization against a reference value or a subtraction of signal intensities.

The determination of a blood flow characteristic can minimally require computer learning model prediction of an area under a time-enhancement curve and may optionally include computer prediction of other parameters such as a time rate of change of a parameter including for example, time rate of change of signal intensity, time rate of change of enhancement, time rate of change tracer mass, time rate of change of flow velocity, time rate of change of flow pressure, and the like. The various time rate of change parameters are related as described in mathematical derivations provided in co-owned PCT/CA2019/050668 filed 16 May 2019 or in co-owned PCT/CA2021/051189 filed 26 Aug. 2021.

Assessment of blood flow and determination of a blood flow characteristic can provide a diagnostic result. For example, predicting an area under time-enhancement curves at first and second sampling sites (or first and second ROIs in the same sampling slice) yields a first area under a time-enhancement curve and a second area under a time-enhancement curve; and estimating of the blood flow characteristic comprises a determination including corresponding values calculated from the first and second areas under time-enhancement curves. As another example, a relative flow velocity or absolute flow velocity may be determined at one or more ROIs. The blood flow characteristic value may in itself provide a diagnostic result. In further examples, corresponding values calculated from the first and second time-enhancement curves or first and second flow velocities are compared and a difference in the corresponding values beyond a predetermined threshold is indicative of a diagnostic result. Thresholds and corresponding diagnostic results can be adopted from relevant literature and medical guidelines. Furthermore, with repeated use of the blood flow imaging method and system, various correlations of metrics, thresholds and diagnostic results may be developed.

A region of interest (ROI) is an area on a digital image that circumscribes or encompasses a desired anatomical location, for example a blood vessel of interest or a portion of a lumen of a blood vessel of interest or heart chamber of interest or any other cardiovasculature of interest. The terms ROI and target voxel or target pixels are related as the ROI defines an area that encompasses one or more voxels (in 3D imaging) or one or more pixels (in 2D imaging). The terms voxel and pixel are related in that both rely on pixel data, but voxel is a 3D-analog of pixel and is an accumulation of pixel data from multiple slices in a 3D image.

Image processing systems permit extraction of pixel data from ROI on images, including for example an average parametric value computed for all pixels within the ROI. A sampling site is the location of one or more imaging slices selected to assess a desired anatomical location, such as a blood vessel of interest or heart chamber of interest or any other cardiovasculature of interest. In some examples, analysis of a time-enhancement curve from a single ROI may be sufficient to determine a blood flow characteristic or metric. In other examples, a plurality of ROIs in a single sampling site or a plurality of ROIs in a plurality of sampling sites, or a plurality imaging slices may be analyzed to obtain a plurality of corresponding image sets and to generate a plurality of corresponding time-enhancement curves, and any number of the plurality of corresponding time-enhancement curves may be compared to determine a blood flow characteristic or blood flow metric. Conventional scanners can capture 3D image data for all or part of a blood vessel of interest or other cardiovasculature of interest, and possibly even all or parts of a plurality of vascular structures such as a plurality of blood vessels of interest. Furthermore, a scan can be subdivided into a plurality of slices as desired, and therefore interrogation of multiple sites or slices at an ROI, near an ROI, upstream of an ROI, downstream of any ROI, or any combination thereof, is feasible and convenient. In multi-slice or multi-site imaging modalities, simultaneous tomographic slices or sampling sites may be extracted per scan. Thus, the blood flow imaging method need not be limited to analysis of one or two time-enhancement curves for a scan of a contrast agent transit (entry to clearance) at blood vessel interest and a single scanning procedure with a single bolus injection of contrast agent can support a plurality of slices or sampling sites divided from the scan data as desired.

Motion correction or motion compensation processing of reconstructed image data may be used if ROIs benefit from adjustment to accommodate the movement of the vessel wall during the cardiac cycle. Rules-based or machine learned motion correction or compensation models are available, and may be used as desired for specific implementations.

A cardiovasculature of interest (also referred to as vascular structure of interest) may be any blood flow passage or lumen of the cardiovascular system (also referred to as the circulatory system), and may include any blood vessel of interest (including for example systemic arteries, peripheral arteries, coronary arteries, pulmonary arteries, carotid arteries, systemic veins, peripheral veins, coronary veins, pulmonary veins) or any heart chamber of interest or any heart aperture of interest that can be imaged by a contrast-enhanced imaging technique. The cardiovasculature of interest will typically have a diameter of at least about 0.1 mm, for example a diameter greater than 0.2 mm or a diameter greater than 0.3 mm. The cardiovasculature of interest, such as a blood vessel of interest or a designated portion of the blood vessel of interest, may be identified and targeted for contrast enhanced blood flow imaging to determine a diagnosis of a cardiovascular disorder or a blood vessel disorder or to determine a predisposition to such disorder. A blood vessel of interest can be within any anatomical area or any organ (for example, brain, lung, heart, liver, kidney and the like) in an animal body (for example, a human body).

The blood flow imaging method is not limited to scan data acquired while a subject is in a hyperemic state (also referred to as hyperemic stress or vasodilatory stress) and time-enhancement curves generated from scan data acquired while a subject is in a non-hyperemic state (also referred to as a resting state) can produce a useful result. Inducing a hyperemic state is a well-known medical protocol in blood flow assessment and often includes administration of a vasodilator such as adenosine, sodium nitroprusside, dipyridamole, regadenoson, or nitroglycerin. Mode of administration of the vasodilator may vary depending on an imaging protocol and can include intravenous or intracoronary injection.

To determine a presence of a cardiovascular disorder at a cardiovasculature of interest, such as a blood vessel disorder at a blood vessel of interest, a blood flow characteristic will be analyzed based on at least one area under a time-enhancement curve, including for example a single area under a time-enhancement curve generated from pixel data of an ROI in a scan of a single sampling site, or as another example a plurality of areas under time-enhancement curves respectively generated from a corresponding plurality of sampling sites. In a case of stenosis a comparison of two sampling sites is beneficial to compare a blood flow characteristic determined at a sampling site upstream of the stenosis with a blood flow characteristic determined at a sampling site downstream of the stenosis. More generally, when a blood vessel of interest is identified, a plurality of sampling sites may be designated at or near the blood vessel of interest; a time-enhancement curve generated for each of the plurality of sampling sites; a desired blood flow characteristic based on a respective time-enhancement curve determined for each of the plurality of sampling sites; and comparing the determined blood flow characteristic of each of the plurality of sampling sites to determine a blood vessel disorder. Depending on a specific implementation determining of a blood flow characteristic at one or more sampling sites or determining presence of absence of a blood vessel disorder based on a comparison of blood flow characteristic at a plurality of sampling sites can provide a diagnostic result.

A cardiovascular disorder or a blood vessel disorder (may also be referred to as a vascular disorder) assessed by the method or system described herein can be any unhealthy blood flow aberration such as a functionally significant blood flow restriction or blood flow obstruction in a cardiac or non-cardiac blood vessel or any aberrant blood flow in a heart chamber or heart aperture that can compromise health of a subject including for example, unhealthy blood flow aberrations symptomatic of Heart Chamber Abnormalities, Heart Valve Abnormalities (eg., Aortic Valve Disease), Heart Failure, Atherosclerosis (for example, plaque formation), Carotid Artery Disease, Peripheral Artery Disease including Renal Artery Disease, Aneurysm, Raynaud's Phenomenon (Raynaud's Disease or Raynaud's Syndrome), Buerger's Disease, Peripheral Venous Disease and Varicose Veins, Thrombosis and Embolism (for example, blood clots in veins), Blood Clotting Disorders, Ischemia, Angina, Heat Attack, Stroke and Lymphedema.

The blood flow imaging method and system can be used to assess a suspected cardiovascular disorder or blood flow disorder, for example by providing a determination of a blood flow characteristic at a blood vessel of interest identified in a previous medical examination as possible source of an unhealthy blood flow aberration. Additionally, due in part to scan data capturing multiple blood vessels and the reduced time to process scan data, the blood flow imaging method and system may be used in a first instance to proactively assess blood flow in a specific blood vessel or specific group of blood vessels (for example, a pulmonary artery blood flow assessment) and may be implemented as a screening tool to be an initial indicator to identify a source of unhealthy blood flow aberration such as a functionally significant stenosis.

The blood flow imaging method does not require the scanned subject or patient to hold breath during a scan procedure. Breath-hold is an option in some examples. In other examples, motion correction or motion compensation processing of image data may be used for scan data acquired without breath-hold of the subject or patient. If desired, motion correction or motion compensation processing of image data may be used for scan data acquired with breath-hold, if ROIs benefit from adjustment to accommodate the movement of the vessel wall during the cardiac cycle. Rules-based or machine learned motion correction or compensation models may be used as desired for specific implementations.

Embodiments disclosed herein, or portions thereof, can be implemented by programming one or more computer systems or devices with computer-executable instructions embodied in a non-transitory computer-readable medium. When executed by a processor, these instructions operate to cause these computer systems and devices to perform one or more functions particular to embodiments disclosed herein. Programming techniques, computer languages, devices, and computer-readable media necessary to accomplish this are known in the art.

In an example, a non-transitory computer readable medium embodying a computer program for blood flow imaging may comprise: computer program code for obtaining image data comprising a plurality of corresponding images capturing at least a portion of one or both an increase phase and a decline phase of a contrast agent in a cardiovasculature of interest; computer program code for providing the image data or image features to a machine learning model to predict an area under a time-enhancement curve of the contrast agent within the cardiovasculature of interest; computer program code for selecting a region of interest within the cardiovasculature of interest in the image data; and computer program code for determining a blood flow characteristic through the region of interest based on the area under the time-enhancement curve. In another related example, the image data comprises at least one image capturing the cardiovasculature of interest prior to entry of the contrast agent. In still another related example, the computer readable medium further comprises computer program code for acquiring scan data of the cardiovasculature of interest from a X-ray based scan or a MRI scan, and reconstructing image data based on the scan data.

The computer readable medium is a data storage device that can store data, which can thereafter, be read by a computer system. Examples of a computer readable medium include read-only memory, random-access memory, CD-ROMs, magnetic tape, optical data storage devices and the like. The computer readable medium may be geographically localized or may be distributed over a network coupled computer system so that the computer readable code is stored and executed in a distributed fashion.

Computer-implementation of the system or method typically comprises a memory, an interface and a processor. The types and arrangements of memory, interface and processor may be varied according to implementations. For example, the interface may include a software interface that communicates with an end-user computing device through an Internet connection. The interface may also include a physical electronic device configured to receive requests or queries from a device sending digital and/or analog information. In other examples, the interface can include a physical electronic device configured to receive signals and/or data relating to the blood flow imaging method and system, for example from an imaging scanner or image processing device.

The technology area of medical imaging, and particularly CT or MRI imaging described herein came into existence as a result of commercially available computers, and moreover required significant advances in semiconductor technology to achieve an implementation in a medical clinic. For CT, implementation in a medical clinic was initiated in the 1970s, while for MRI medical imaging implementation was initiated in the 1980s.

As such, CT or MRI imaging is intimately tied to computers and computer function, and CT or MRI images are communicated and processed using specialized medical imaging software to process and extract data points to generate time-enhancement curves. For example, CT or MRI image data can have a range greater than 1000 pixel/voxel values (continuous, not discretized) that make it impossible for human experts to accurately quantify enhancement. In addition, CT or MRI image data are stored and processed in DICOM format requiring specialized software to assess enhancement and time information to accurately generate a time-enhancement curve. Neither the time component nor the enhancement component of the time-enhancement curve is assessed and quantified without specialized software.

Any suitable processor type may be used depending on a specific implementation, including for example, a microprocessor, a programmable logic controller or a field programmable logic array. Moreover, any conventional computer architecture may be used for computer-implementation of the system or method including for example a memory, a mass storage device, a processor (CPU), a graphical processing unit (GPU), a Read-Only Memory (ROM), and a Random-Access Memory (RAM) generally connected to a system bus of data-processing apparatus. Memory can be implemented as a ROM, RAM, a combination thereof, or simply a general memory unit. Software modules in the form of routines and/or subroutines for carrying out features of the system or method can be stored within memory and then retrieved and processed via processor to perform a particular task or function. Similarly, one or more method steps may be encoded as a program component, stored as executable instructions within memory and then retrieved and processed via a processor. A user input device, such as a keyboard, mouse, or another pointing device, can be connected to PCI (Peripheral Component Interconnect) bus. If desired, the software may provide an environment that represents programs, files, options, and so forth by means of graphically displayed icons, menus, and dialog boxes on a computer monitor screen. For example, any number of blood flow images and blood flow characteristics may be displayed, including for example a time-enhancement curve.

Computer-implementation of the system or method may accommodate any type of end-user computing device including computing devices communicating over a networked connection. The computing device may display graphical interface elements for performing the various functions of the system or method, including for example display of a blood flow characteristic determined for a cardiovasculature of interest. For example, the computing device may be a server, desktop, laptop, notebook, tablet, personal digital assistant (PDA), PDA phone or smartphone, and the like. The computing device may be implemented using any appropriate combination of hardware and/or software configured for wired and/or wireless communication. Communication can occur over a network, for example, where remote control of the system is desired.

If a networked connection is desired the system or method may accommodate any type of network. The network may be a single network or a combination of multiple networks. For example, the network may include the internet and/or one or more intranets, landline networks, wireless networks, and/or other appropriate types of communication networks. In another example, the network may comprise a wireless telecommunications network (e.g., cellular phone network) adapted to communicate with other communication networks, such as the Internet. For example, the network may comprise a computer network that makes use of a TCP/IP protocol (including protocols based on TCP/IP protocol, such as HTTP, HTTPS or FTP).

Embodiments described herein are intended for illustrative purposes without any intended loss of generality. Still further variants, modifications and combinations thereof are contemplated and will be recognized by the person of skill in the art. Accordingly, the foregoing detailed description is not intended to limit scope, applicability, or configuration of claimed subject matter.

What is claimed is:

1. A computer implemented method for blood flow imaging comprising:
   obtaining CT or MRI image data comprising a plurality of corresponding images capturing at least a portion of one or both an increase phase and a decline phase of a contrast agent in a cardiovasculature of interest;
   extracting a first image feature of a measured time-enhancement curve from the CT or MRI image data;
   providing the first image feature and at least one non-image feature to a machine learning model to generate a predicted value of an area under a simulated time-enhancement curve of the contrast agent within the cardiovasculature of interest, the predicted value simulating a second set of image acquisition parameters that are different than a first set of image acquisition parameters used to acquire the CT or MRI image data;

converting the predicted value of area under the simulated time-enhancement curve to a total sum of contrast agent concentration time product in the cardiovasculature of interest;

determining a blood flow characteristic in the cardiovasculature of interest based on a ratio of mass of the contrast agent in the cardiovasculature of interest to a total sum of contrast agent concentration time product in the cardiovasculature of interest.

2. The method of claim 1, further comprising including a baseline data point extracted from the CT or MRI image data in the measured time-enhancement curve, the CT or MRI image data comprises at least one image capturing the cardiovasculature of interest prior to entry of the contrast agent to provide the baseline data point.

3. The method of claim 1, wherein the machine learning model is trained with training inputs of the image feature of the measured time-enhancement curve and at least one non-image feature, and associated with a ground truth value of an expected area under the simulated time-enhancement curve.

4. The method of claim 1, wherein the image feature is an at least partial time-enhancement curve and extracting the image feature comprises: generating the at least partial time-enhancement curve of the contrast agent based on the image data, the at least partial time-enhancement curve having at least an upslope or a downslope.

5. The method of claim 1, wherein the image feature is a measured value of an area under an at least partial time-enhancement curve and extracting the image feature comprises: generating the at least partial time-enhancement curve of the contrast agent based on the image data, the at least partial time-enhancement curve having at least an upslope or a downslope; and calculating the area under the at least partial time-enhancement curve.

6. The method of claim 1, further comprising providing a second image feature based on enhancement of signal intensity, thickness of a wall of a cardiovasculature of interest, size of a cardiovasculature of interest, diameter of a cardiovasculature of interest, morphology of a cardiovasculature of interest, location of sampling site in a cardiovascular of interest, or degree of stenosis in a cardiovasculature of interest.

7. The method of claim 1, wherein the non-image feature is based on age, sex, weight, heart rate, blood pressure, x-ray tube voltage, x-ray tube current, gradient pulse sequence, disease state, contrast-injection rate, contrast agent volume, or contrast agent concentration.

8. The method of claim 1, wherein the first set of image acquisition parameters is different than the simulated second set of image acquisition parameters according to at least one parameter selected from the group consisting of: scan axis orientation relative to a longitudinal axis of the cardiovasculature of interest, anatomical location of scan, hyperemic or rest condition of a subject, time duration of scan, x-ray tube voltage, x-ray tube current, gradient pulse sequence, contrast-injection rate, contrast agent volume, or contrast agent concentration.

9. The method of claim 1, wherein determining the blood flow characteristic comprises determining an absolute flow velocity using Reynolds transport theorem by determining a time rate of change of contrast agent mass in the cardiovasculature of interest based on a time rate of change of signal enhancement measured from an at least partial time-enhancement curve, a factor for converting signal enhancement to contrast agent concentration, a predetermined volume value of injected contrast agent, and a time value of a duration of time that signal intensity is higher than a predetermined baseline threshold level;

determining density of the contrast agent in the cardiovasculature of interest based on the ratio defined in claim 1, a time value of a duration of time that signal intensity is higher than a predetermined baseline threshold level, and the mass of contrast agent in the cardiovasculature of interest; and determining an area measured from the image data in the cardiovasculature of interest.

10. The method of claim 1, wherein determining the blood flow characteristic comprises determining a flow pressure by applying Bernoulli's equation expressed as $$P_A + \tfrac{1}{2}\rho V_A^2 + \rho g h_A = P_B + \tfrac{1}{2}\rho V_B^2 + \rho g h_B + P_L.$$

11. A system for blood flow imaging comprising:
a memory for storing CT or MRI image data comprising a plurality of corresponding images capturing at least a portion of one or both an increase phase and a decline phase of a contrast agent in a cardiovasculature of interest;

a CT or MRI image processing component to extract a first image feature of a measured time-enhancement curve from the CT or MRI image data;

a machine learning model to generate a predicted value of an area under a simulated time-enhancement curve of the contrast agent within the cardiovasculature of interest by inputting the first image feature and at least one non-image feature to the machine learning model, the predicted value simulating a second set of image acquisition parameters that are different than a first set of image acquisition parameters used to acquire the CT or MRI image data;

and a processor executing instructions to communicate with the CT or MRI image processing component and the machine learning model, and convert the predicted value of area under the simulated time-enhancement curve to a total sum of contrast agent concentration time product in the cardiovasculature of interest, and determine a blood flow characteristic in the cardiovasculature of interest based on a ratio of mass of the contrast agent in the cardiovasculature of interest to the a total sum of contrast agent concentration time product in the cardiovasculature of interest.

12. The system of claim 11, further comprising including a baseline data point extracted from the CT or MRI image data in the measured time-enhancement curve, the CT or MRI image data comprises at least one image capturing the cardiovasculature of interest prior to entry of the contrast agent to provide the baseline data point.

13. The system of claim 11, wherein the machine learning model is trained with training inputs of the image feature of the measured time-enhancement curve and at least one non-image feature, and associated with a ground truth value of an expected area under the simulated time-enhancement curve.

14. The system of claim 11, wherein the image feature is an at least partial time-enhancement curve and extracting the image feature comprises: generating the at least partial time-enhancement curve of the contrast agent based on the image data, the at least partial time-enhancement curve having at least an upslope or a downslope.

15. The system of claim 11, wherein the image feature is a measured value of an area under an at least partial time-enhancement curve and extracting the image feature comprises: generating the at least partial time-enhancement curve of the contrast agent based on the image data, the at least partial time-enhancement curve having at least an upslope or a downslope; and calculating the area under the at least partial time-enhancement curve.

16. The system of claim 11, further comprising providing a second image feature based on enhancement of signal intensity, thickness of a wall of a cardiovasculature of interest, size of a cardiovasculature of interest, diameter of a cardiovasculature of interest, morphology of a cardiovasculature of interest, location of sampling site in a cardiovascular of interest, or degree of stenosis in a cardiovasculature of interest.

17. The system of claim 11, wherein the non-image feature is based on age, sex, weight, heart rate, blood pressure, x-ray tube voltage, x-ray tube current, gradient pulse sequence, disease state, contrast-injection rate, contrast agent volume, or contrast agent concentration.

18. The system of claim 11, wherein the first set of image acquisition parameters is different than the simulated second set of image acquisition parameters according to at least one parameter selected from the group consisting of: scan axis orientation relative to a longitudinal axis of the cardiovasculature of interest, anatomical location of scan, hyperemic or rest condition of a subject, time duration of scan, x-ray tube voltage, x-ray tube current, gradient pulse sequence, contrast-injection rate, contrast agent volume, or contrast agent concentration.

19. The system of claim 11, wherein the processor executes instructions to determine the blood flow characteristic comprises determining an absolute flow velocity using Reynolds transport theorem by determining a time rate of change of contrast agent mass in the cardiovasculature of interest based on a time rate of change of signal enhancement measured from an at least partial time-enhancement curve, a factor for converting signal enhancement to contrast agent concentration, a predetermined volume value of injected contrast agent, and a time value of a duration of time that signal intensity is higher than a predetermined baseline threshold level;

determining density of the contrast agent in the cardiovasculature of interest based on a ratio of mass of the contrast agent in the cardiovasculature of interest to a total sum of contrast agent concentration time product in the cardiovasculature of interest, a time value of a duration of time that signal intensity is higher than a predetermined baseline threshold level, and the mass of contrast agent in the cardiovasculature of interest; and determining an area measured from the image data in the cardiovasculature of interest.

20. The system of claim 11, wherein the processor executes instructions to determine the blood flow characteristic comprises determining a flow pressure by applying Bernoulli's equation expressed as:

$$P_A + \tfrac{1}{2}\rho V_A^2 + \rho g h_A = P_B + \tfrac{1}{2}\rho V_B^2 + \rho g h_B + P_L.$$

* * * * *